US011571431B2

(12) United States Patent
Baharaff et al.

(10) Patent No.: US 11,571,431 B2
(45) Date of Patent: *Feb. 7, 2023

(54) ARAMCHOL SALTS

(71) Applicant: GALMED RESEARCH AND DEVELOPMENT LTD, Tel Aviv (IL)

(72) Inventors: Allen Baharaff, Tel Aviv (IL); Idit Eshkar-Oren, Tel Aviv (IL)

(73) Assignee: Galmed Research and Development Ltd, Tel Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/509,004

(22) Filed: Oct. 24, 2021

(65) Prior Publication Data

US 2022/0040204 A1 Feb. 10, 2022

Related U.S. Application Data

(63) Continuation of application No. 17/082,052, filed on Oct. 28, 2020, which is a continuation of application No. 15/580,611, filed as application No. PCT/IL2016/050595 on Jun. 8, 2016, now Pat. No. 10,849,911, application No. 17/509,004, filed on Oct. 24, 2021, which is a continuation-in-part of application No. 15/100,993, filed as application No. PCT/IL2014/051052 on Dec. 4, 2014.

(60) Provisional application No. 62/173,390, filed on Jun. 10, 2015, provisional application No. 61/911,478, filed on Dec. 4, 2013.

(51) Int. Cl.
*A61K 31/575* (2006.01)
*A61K 9/00* (2006.01)

(52) U.S. Cl.
CPC .......... *A61K 31/575* (2013.01); *A61K 9/0053* (2013.01); *C07B 2200/13* (2013.01)

(58) Field of Classification Search
CPC .................................................... A61K 31/575
See application file for complete search history.

(56) References Cited

U.S. PATENT DOCUMENTS

| | | | |
|---|---|---|---|
| 2,252,863 | A | 8/1941 | Raymond et al. |
| 4,022,806 | A | 1/1977 | Frost |
| 4,377,583 | A * | 3/1983 | Larsen ................. C07D 495/04 544/278 |
| 5,512,558 | A | 4/1996 | Enhsen |
| 6,395,722 | B1 | 5/2002 | Gilat |
| 6,384,024 | B1 | 7/2002 | Gilat |
| 6,642,268 | B2 | 1/2003 | Keller |
| 6,589,946 | B2 | 8/2003 | Gilat |
| 7,501,403 | B2 | 10/2009 | Gilat |
| 8,110,564 | B2 | 7/2012 | Gilat |
| 8,975,246 | B2 | 3/2015 | Gilat |
| 10,266,560 | B2 | 4/2019 | Or |
| 2008/0064888 | A1 | 1/2008 | Allegrini et al. |
| 2009/0149537 | A1 | 6/2009 | Gilat |
| 2012/0277448 | A1 | 1/2012 | Jiang |
| 2012/0157419 | A1 | 6/2012 | Gilat et al. |
| 2012/0214872 | A1 | 8/2012 | Gilat |
| 2012/0264824 | A1 | 10/2012 | Mizuguchi et al. |
| 2016/0175223 | A1 | 6/2016 | Dayan et al. |
| 2016/0175324 | A1 | 6/2016 | Dayan et al. |
| 2017/0196891 | A1 | 7/2017 | Halpern et al. |
| 2017/0362211 | A1 | 12/2017 | Iairson |
| 2018/0125862 | A1 | 5/2018 | Hayadeny-Nissimov et al. |
| 2019/0175619 | A1 | 6/2019 | Hayadeny-Nissimov et al. |

FOREIGN PATENT DOCUMENTS

| | | |
|---|---|---|
| JP | 2003-516317 | 4/2001 |
| JP | 2007-534757 | 10/2005 |
| WO | WO1999/052932 | 10/1999 |
| WO | WO2002/083147 | 10/2002 |
| WO | WO2009/060452 | 5/2009 |
| WO | 2010/086864 | * 5/2010 |
| WO | WO2010/086864 | 5/2010 |
| WO | WO2011/038207 | 3/2011 |
| WO | PCT/JP2011/074607 | 6/2011 |
| WO | WO2011/097079 | 8/2011 |
| WO | WO2015/019358 | 2/2015 |
| WO | WO2015/019359 | 2/2015 |
| WO | WO2015/186126 | 12/2015 |
| WO | WO2016/112305 | 7/2016 |
| WO | WO2016/199137 | 12/2016 |
| WO | WO2017/017677 | 2/2017 |
| WO | WO2017/125929 | 7/2017 |
| WO | WO2017/210526 | 7/2017 |
| WO | WO2018/051180 | 3/2018 |

OTHER PUBLICATIONS

Lange et al. "Soluble Steroids I: Sugar Derivatives" Journal of pharmaceutical sciences. Nov. 1, 1962;51(11):1102-6.
Study of Aramchol in Patients with Fatty Liver Disease or Nonalcoholic Steathepatitis (Aramchol003), Jan. 30, 2002; Nat Inst of health, Clinical Trials.gov.
Aitipamula et al. "Polymorphs, salts, and cocrystals: what's in a name?" Crystal growth & design. Apr. 19, 2012;12(5):2147-52.
Clinicaltrials.gov "A Phase 1 Single and Multiple-Dose Study of Aramchol in Healthy Male volunteers" National Library of Medicine NCT 00776841, updated Nov. 2, 2010.
Clinicaltrials.gov "Pharmacokinetics of single and Multiple Escalating Doses of Aramchol and Food Effect in Healthy Volunteers" National Library of Medicine NCT02374437, updated Feb. 26, 2015.
ISR—dated Mar. 4, 2015 in connection with PCT/IL2014/051052.
Written Opinion—dated Mar. 4, 2015 in connection with PCT/IL2014/051052.
International Preliminary Report on Patentability—dated Jun. 7, 2016 in connection with PCT/IL2014/051052.
ISR dated Sep. 25, 2016 in connection with PCT/IL2016/050595.
Written Opinion—dated Sep. 25, 2016 in connection with PCT/IL2016/050595.

(Continued)

*Primary Examiner* — Rei Tsang Shiao
(74) *Attorney, Agent, or Firm* — Mark S. Cohen; Pearl Cohen Zedek Latzer Baratz LLP

(57) ABSTRACT

The present invention relates to salts of arachidyl amido cholanoic acid (Aramchol), pharmaceutical compositions comprising Aramchol salts, methods for their preparation, and methods of use thereof in medical treatment.

13 Claims, 9 Drawing Sheets

(56) References Cited

OTHER PUBLICATIONS

R.R. Remshaw p. 128, 1910 Organic and Biological 892.
Stahl. "Preparation of Water Soluble Compounds Through Salt Formation" The practice of medicinal chemistry, Chapter 35; Second Edition, pp. 601-615; ISBN 0-12-744481-5, XP002566271.
Clinicaltrials.gov [Internet] "A Clinical Trial to Evaluate the Efficacy and Safety of Two Aramchol Doses Versus Placebo in Patient with NASH", National Library of Medicine NCT02279524, updated Oct. 30, 2014, available online at: , https://clinicaltrials.gov/archive/NCT02279524/2014_10_30.
Clinicaltrials.gov [Internet] "A Clinical Trial to Evaluate the Efficacy and Safety of Two Aramchol Doses Versus Placebo in Patient with NASH", National Library of Medicine NCT02279524, updated Nov. 2, 2015, available online at: https://clinicaltrials.gov/archive/NC002279524/2015_11_02.
Non-alcoholic fatty liver disease Wikipedia 2018.
Safadi et al. "The fatty acid-bile acid conjugate aramchol reduces liver fat content in patients with nonalcoholic fatty liver disease" Clinical Gastroenterology and Hepatology. Dec. 1, 2014;12(12):2085-91.
Singh et al. "Fibrosis progression in nonalcoholic fatty liver vs nonalcoholic steatohepatitis: a systematic review and meta-analysis of paired-biopsy studies" Clinical Gastroenterology and Hepatology. Apr. 1, 2015;13(4):643-54.

M. Iruarrizaga-Lejarreta et al; Role of Aramchol in Steatohepatitis and Fibrosis in Mice; Hepatology Communications, vol. 1, No. 9, Nov. 3, 2017 (Nov. 3, 2017) p. 911-927. XP002778683.
Corsetti et al; Int J Immunopathol Pharmacol 2011; 24(3); 611-9.
Sachan et al; Am J Clin Nutr 1984, 39(5) 738-44.
Helton et al., J Surg Res., 1990 48(4): 297-303.
Ayesha Jacob et al; (DOI: 10.1039/C2CE26706C (Paper) CrystEngcomm, 2013, 15, 931-939).
International Preliminary Report on Patentability, dated May 20, 2021 in connection with PCT International Application No. PCT/IL2019/051121.
Safadi Rifaat et al; One year results of the global phase 2b Randomized placebo-controlled Arrest Trial of Aramchol, a Stearoyl CoA Desaturase Inhibitor, in patients with Nash; Hepatology, vol. 68 No. 1 Oct. 2018 p. 1447-1448.
Trovato, F. M., Catalano, D., Musumeci, G., & Trovato, G. M. (2014). 4Ps medicine of the fatty liver: the research model of predictive, preventive, personalized and participatory medicine—recommendations for facing obesity, fatty liver and fibrosis epidemics. EPMA Journal, 5(1), 1-24.
Ayesha Jacobs et al (28th European Crystallographic Meeting, ECM 28, UK, 2013 Acta Cryst. (2013). A69, s645; Aug. 2013; Acta Crystallographica Section A Foundations of Crystallography 69(a1):s645-s645, DOI:10.1107/SO 10876731309435X, Salts of (+)-deoxycholic acid with amines: structure and chiral resolution).
"Medicinal Basic Chemistry" chiefly-edited by Zhang Yaowu, People's Military Medical Press. pp. 293-294 "(2) Chemical properties of carboxylic acids" May 2012.

\* cited by examiner

ARAMCHOL SALTS

CROSS REFERENCE TO RELATED APPLICATIONS

This application is a Continuation application of U.S. application Ser. No. 15/580,611, which is a National Phase Application of PCT International Application No. PCT/IL2016/050595, International Filing Date Jun. 8, 2016, claiming the benefit of U.S. Provisional Application No. 62/173,390, filed Jun. 10, 2015; and a Continuation in Parts application of U.S. application Ser. No. 15/100,993, which is a National Phase Application of PCT International Application No. PCT/IL2014/051052, International Filing Date Apr. 12, 2014, claiming the benefit of U.S. Provisional Application No. 61/911,478, filed Dec. 4, 2013; which are hereby incorporated by reference.

FIELD OF THE INVENTION

The present invention relates to unit dosage forms of readily bioavailable amine salts of arachidyl amido cholanoic acid (Aramchol) and use thereof in medical treatment.

BACKGROUND OF THE INVENTION

Aramchol is an amide conjugate of arachidic acid and 3-aminocholic acid, effective in reducing liver fat content as well as improving metabolic parameters associated with fatty liver disease. It belongs to a family of synthetic Fatty-Acid/Bile-Acid Conjugates (FABACs) and is being developed as a potentially disease modifying treatment for fatty liver disease and Non Alcoholic SteatoHepatitis (NASH).

Aramchol is chemically named 3β-arachidylamido-7α,12α-dihydroxy-5β-cholan-24-oic acid, and is represented by the following chemical structure:

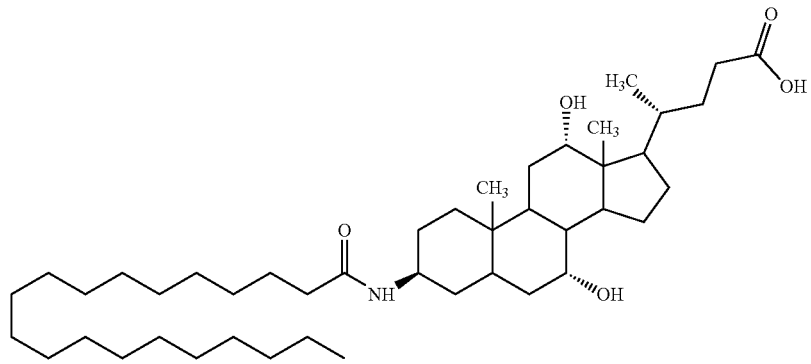 [SMILES: CCCCCCCCCCCCCCCCCCCC(=O)N[C@H]1CCC2(C)C(C1)C[C@@H](O)C1C2C[C@H](O)C2(C)C1CCC2[C@H](C)CCC(=O)O]

Aramchol, processes for its preparation, and use thereof are disclosed in U.S. Pat. Nos. 6,384,024; 6,395,722; 6,589,946; 7,501,403; 8,110,564; U.S. 2012/0214872; and WO 2009/060452.

There remains an unmet need for new forms of Aramchol having desirable physiochemical properties. In addition, unit dosage forms of Aramchol salts having improved clinical properties, are further required.

SUMMARY OF THE INVENTION

The present invention relates to salts of Aramchol, for example, salts with amino alcohols, amino sugars or amino acids. Specifically, the invention provides new unit dosage forms comprising the Aramchol amine salts, and use thereof in medical treatment.

The present invention is based, in part, on the unexpected finding of new salts of Aramchol having advantageous physicochemical properties. About 30 pharmaceutically acceptable bases were screened in an effort to prepare Aramchol salts with increased solubility. Of these, amine-based salts were found to be suitable and in particular three salts of Aramchol, namely the N-methylglucamine (meglumine), lysine and tromethamine salts have been shown to possess advantageous properties, including increased solubility, as well as increased absorption and exposure, which correlate with higher bioavailability. Thus, the Aramchol salts of the present invention are suitable for pharmaceutical use at lower doses as compared with Aramchol free acid. In addition, the new salts have improved flow properties as compared with Aramchol free acid, and therefore can be more easily processed into solid dosage formulations such as tablets or capsules.

According to certain embodiments, the invention is directed to pharmaceutical compositions in unit dosage form, comprising low doses of Aramchol amine salts, suitable for human administration.

Without being bound to any theory or mechanism, the advantageous physicochemical properties of the new salts of Aramchol, including increased solubility, increased absorption and/or increased exposure, correlate with higher bioavailability of the Aramchol salts, which enable Aramchol to be formulated and prescribed in dosages previously considered insufficiently effective or sub-therapeutic. The findings of the present invention thus revolutionize the field of Aramchol therapy, circumventing the need for high-dose Aramchol formulations and related complications.

According to aspects of the invention, the invention relates to pharmaceutical compositions in unit dosage form comprising a therapeutically effective amount of a salt of 3β-arachidylamido-7α,12α-dihydroxy-5β-cholan-24-oic acid (Aramchol) with an amine, and optionally at least one pharmaceutically acceptable carrier, diluent, vehicle or excipient. The compositions of the invention advantageously contain the active ingredient at surprisingly reduced, yet therapeutically effective amounts, as detailed herein. According to advantageous embodiments of the invention, the therapeutically effective amount of the active ingredient in the composition, namely the Aramchol component (Aramchol carboxylate), may be within the range of about 10 to about 400 mg, based on the weight of Aramchol free acid. Particularly advantageous doses disclosed herein include e.g. doses providing about 10 to 25 mg, about 10 to 100 mg, about 30 to 100 mg, about 30 to 200 mg, about 100 to 200 mg, about 30 to 300 mg, about 100 to 300 mg, about 200 to 300 mg, or about 300 to 400 mg of the active ingredient. Each possibility represents a separate embodiment of the invention.

According to a first aspect, the present invention provides a pharmaceutical composition in unit dosage form comprising a therapeutically effective amount of a salt of 3β-arachidylamido-7α,12α-dihydroxy-5β-cholan-24-oic acid (Aramchol) with an amine, in which the Aramchol component is present in an amount of about 10 to 400 mg; and optionally at least one pharmaceutically acceptable carrier, diluent, vehicle or excipient. According to various advantageous embodiments, the amount of said Aramchol component is selected from the group consisting of (i) about 10 to 25 mg; (ii) about 10 to 100 mg; (iii) about 30 to 100 mg; (iv) about 30 to 200 mg; (v) about 100 to 200 mg; (vi) about 30 to 300 mg; (vii) about 100 to 300 mg; and (viii) about 200 to 300 mg. Each possibility represents a separate embodiment of the invention.

In certain embodiments, the amount of said Aramchol component is 10 to 25 mg. In certain embodiments, the amount of said Aramchol component is 10 to 100 mg. In certain embodiments, the amount of said Aramchol component is 30 to 100 mg. In certain embodiments, the amount of said Aramchol component is 30 to 200 mg. In certain embodiments, the amount of said Aramchol component is 100 to 200 mg. In certain embodiments, the amount of said Aramchol component is 30 to 300 mg. In certain embodiments, the amount of said Aramchol component is 100 to 300 mg. In certain embodiments, the amount of said Aramchol component is 200 to 300 mg. In certain embodiments, the amount of said Aramchol component is 200 to 400 mg.

In some embodiments, the amine is selected from the group consisting of ammonia, a primary amine, a secondary amine, a tertiary amine, a quaternary ammonium compound, an amino alcohol, an amino sugar and an amino acid. Currently preferred salts are Aramchol salts with an amino alcohol, amino sugar or amino acid. Each possibility represents a separate embodiment of the present invention.

In some embodiments, the present invention provides ammonium, benzathine, trimethylglycine (betaine), ethanolamine, diethanolamine, diethylamine, arginine, lysine, choline, deanol, 2-diethylaminoethanol, N-methylglucamine (meglumine), N-ethylglucamine (eglumine) or tromethamine salt of 3β-arachidylamido-7α,12α-dihydroxy-5β-cholan-24-oic acid. Each possibility represents a separate embodiment of the present invention.

In one currently preferred embodiment, the present invention relates to 3β-arachidylamido-7α,12α-dihydroxy-5β-cholan-24-oic acid lysine salt.

In another currently preferred embodiment, the present invention relates to 3β-arachidylamido-7α,12α-dihydroxy-5β-cholan-24-oic acid tromethamine salt.

In another currently preferred embodiment, the present invention relates to 3β-arachidylamido-7α,12α-dihydroxy-5β-cholan-24-oic acid N-methylglucamine salt.

In another embodiment, the salt of 3β-arachidylamido-7α,12α-dihydroxy-5β-cholan-24-oic acid according to the present invention is in a crystalline form. In yet another embodiment, the salt of 3β-arachidylamido-7α,12α-dihydroxy-5β-cholan-24-oic acid according to the present invention is in an amorphous form.

In certain embodiments, the ratio between the 3β-arachidylamido-7α,12α-dihydroxy-5β-cholan-24-oic acid and the amine is from about 1:3 to about 3:1. In certain embodiments, the ratio between the 3β-arachidylamido-7α, 12α-dihydroxy-5β-cholan-24-oic acid and the amine is from about 1:2 to about 2:1. In certain embodiments, the ratio between the 3β-arachidylamido-7α,12α-dihydroxy-5β-cholan-24-oic acid and the amine is about 1:1.

In certain embodiments, the pharmaceutical composition of the present invention is in a form suitable for administering via an oral, transdermal or topical route. In certain embodiments, the pharmaceutical composition of the present invention is in a form suitable for oral administration (e.g. to a human subject). In certain embodiments, the pharmaceutical composition is in a form selected from the group consisting of tablets, pills, capsules, pellets, granules, powders, lozenges, sachets, cachets, patches, elixirs, suspensions, dispersions, emulsions, solutions, syrups, gels, aerosols, ointments, soft and hard gelatin capsules, suppositories, sterile injectable solutions, and sterile packaged powders. In a particular embodiment, said composition is formulated in solid oral dosage form (e.g. tablets, capsules and pills). Each possibility represents a separate embodiment of the present invention.

In other embodiments, the invention provides a pharmaceutical composition according to the invention, for use in the treatment of a disease or condition amenable for treatment by Aramchol in a human subject in need thereof.

In other embodiments, the present invention provides the pharmaceutical composition of the present invention for use in the treatment of conditions associated with fatty liver such as Non Alcoholic SteatoHepatitis (NASH) or other diseases the treatment of which may benefit from modulating cholesterol or lipid balance.

In some embodiments, the pharmaceutical composition of the present invention is for use in dissolving cholesterol gallstones in bile, and/or in preventing formation of such gallstones. In other embodiments, the pharmaceutical composition of the present invention is for use in for treating arteriosclerosis.

In certain embodiment, the pharmaceutical composition of the present invention is for use in treating a disease or disorder associated with altered glucose metabolism. In one embodiment, the disease or disorder associated with altered glucose metabolism is selected from the group consisting of hyperglycemia, diabetes, insulin resistance, and obesity. Each possibility represents a separate embodiment of the present invention.

In other embodiments, the pharmaceutical composition of the present invention is for use in treating, preventing, or inhibiting progression of a brain disease characterized by amyloid plaque deposits. In one embodiment, the brain disease characterized by amyloid plaque deposits is Alzheimer's disease.

The pharmaceutical composition of the present invention can be administered via a route selected from the group consisting of oral, topical, subcutaneous, intraperitoneal, rectal, intravenous, intra-arterial, transdermal, intramuscular, and intranasal. Each possibility represents a separate embodiment of the present invention. In certain embodiments, the pharmaceutical composition of the present invention is in a form suitable for oral administration.

In another aspect there is provided a method of treating a disease or condition amenable for treatment by 3μ-arachidylamido-7α,12α-dihydroxy-5β-cholan-24-oic acid (Aramchol) in a human subject in need thereof, comprising the step of administering to the subject a pharmaceutical composition of the invention.

In another aspect the invention provides a method of treating a condition associated with fatty liver (e.g. Non Alcoholic SteatoHepatitis (NASH)) in a human subject in need thereof, comprising the step of administering to the subject a therapeutically effective amount of a salt of 3β-arachidylamido-7α,12α-dihydroxy-5β-cholan-24-oic acid (Aramchol) with an amine, in which the Aramchol component is present in an amount of about 10 to 400 mg; and optionally at least one pharmaceutically acceptable carrier, diluent, vehicle or excipient. In various advantageous embodiments, the amount of said Aramchol component is selected from the group consisting of (i) about 10 to 25 mg; (ii) about 10 to 100 mg; (iii) about 30 to 100 mg; (iv) about 30 to 200 mg; (v) about 100 to 200 mg; (vi) about 30-300 mg; (vii) about 100-300 mg; (viii) about 200 to 300 mg; and (ix) about 300 to 400 mg. Each possibility represents a separate embodiment of the invention.

In another embodiment the invention provides a method of treating a condition associated with fatty liver in a human subject in need thereof, comprising the step of administering to the subject a pharmaceutical composition in unit dosage form comprising a therapeutically effective amount of a salt of 3β-arachidylamido-7α,12α-dihydroxy-5β-cholan-24-oic acid (Aramchol) with an amine, in which the Aramchol component is present in an amount of about 10 to 400 mg, based on the weight of Aramchol free acid; and optionally at least one pharmaceutically acceptable carrier, diluent, vehicle or excipient. In particular embodiments, the amount of said Aramchol component is selected from the group consisting of (i) 10 to 25 mg; (ii) 10 to 100 mg; (iii) 30 to 100 mg; (iv) 30 to 200 mg; (v) 100 to 200 mg; (vi) 30-300 mg; (vii) 100-300 mg; (viii) 200 to 300 mg; and (ix) 300 to 400 mg.

In various other embodiments, the composition is administered to said subject in a dosage regimen selected from the group consisting of: (i) once a day; (ii) 2 to 4 separate administrations per day; (iii) 2 to 4 separate administrations per week; and (iv) 2 to 4 separate administrations per month.

In another embodiment, a therapeutically effective amount of the salt in which the Aramchol component is present in an amount of 200 to 300 mg is administered daily to said subject. In another embodiment a therapeutically effective amount of the salt in which the Aramchol component is present in an amount of about 260 mg is administered daily to said subject. In another embodiment a therapeutically effective amount of the salt in which the Aramchol component is present in an amount of 300 to 400 mg is administered daily to said subject. In another embodiment, a therapeutically effective amount of the salt in which the Aramchol component is present in an amount of about 400 mg is administered daily to said subject.

In another embodiment, said composition is formulated as a solid oral dosage form.

In some embodiments, the present invention provides a method of reducing cholesterol levels in the blood, or treating fatty liver, or treating NASH, or dissolving cholesterol gallstones in bile, or preventing formation of such gallstones, or treating arteriosclerosis, comprising administering to a human subject in need thereof a pharmaceutical composition of the invention. Each possibility represents a separate embodiment of the invention. In a particular embodiment, the method is for treating Non Alcoholic SteatoHepatitis (NASH) in said subject.

In certain embodiments, the present invention provides a method of treating a disease or disorder associated with altered glucose metabolism comprising administering to said subject a pharmaceutical composition of the invention. In further embodiments, the present invention provides a method of treating, preventing, or inhibiting progression of a brain disease characterized by amyloid plaque deposits, comprising administering to a human subject in need thereof a pharmaceutical composition of the invention.

In another aspect, the invention relates to the use of the pharmaceutical composition of the present invention for the preparation of a medicament for treating a disease or condition amenable for treatment by Aramchol in a human subject in need thereof. According to particular embodiments, the disease or condition is selected from the group consisting of conditions associated with fatty liver, high cholesterol levels in the blood, altered glucose metabolism, gallstones, amyloid plaque deposits and arteriosclerosis. In other embodiments, the amount of the Aramchol component in said medicament is selected from the group consisting of (i) 10 to 25 mg; (ii) 10 to 100 mg; (iii) 30 to 100 mg; (iv) 30 to 200 mg; (v) 100 to 200 mg; (vi) 30-300 mg; (vii) 100-300 mg; (viii) 200 to 300 mg; and (ix) 300 to 400 mg. Each possibility represents a separate embodiment of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
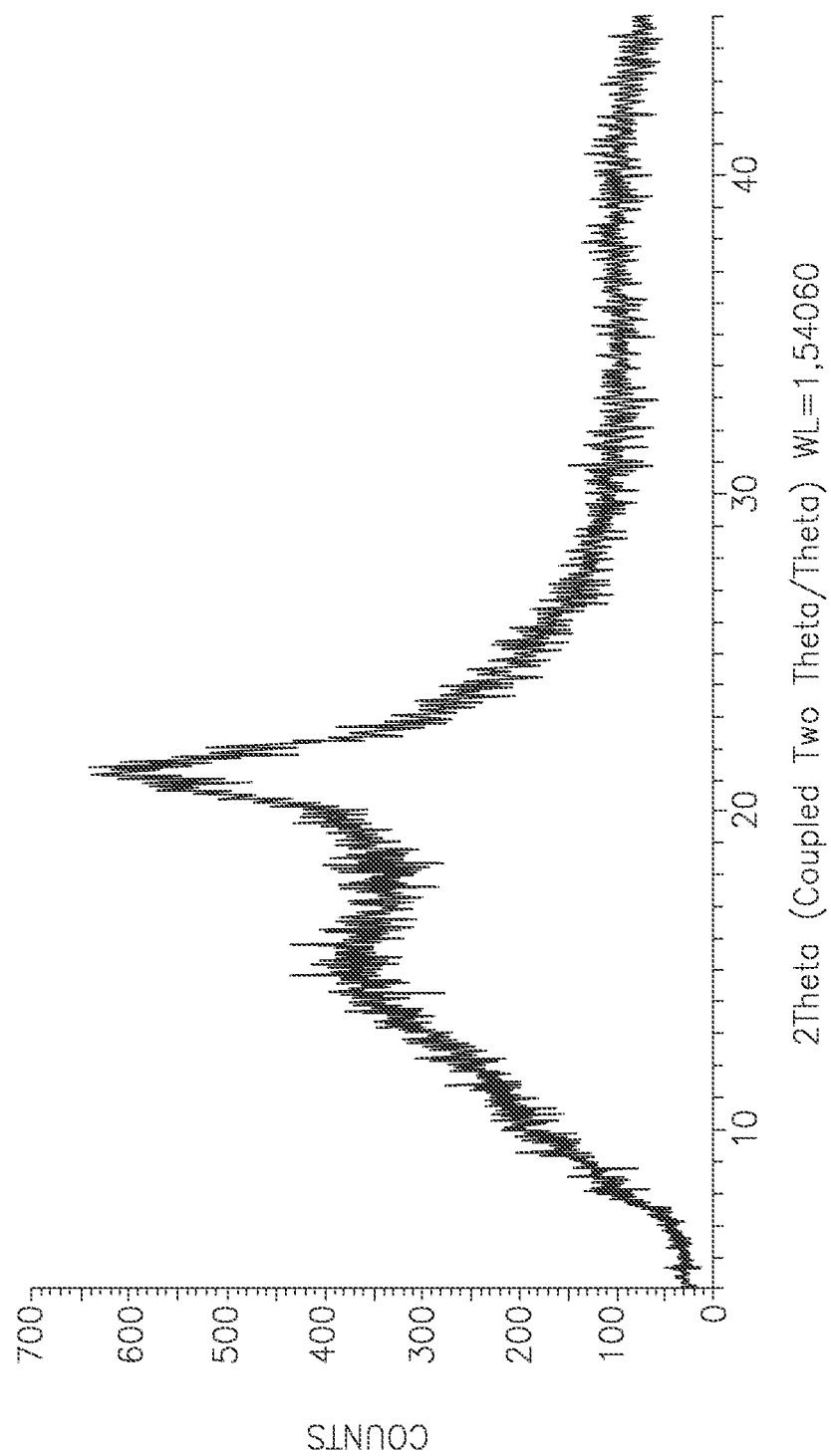
FIG. 1 illustrates a characteristic X-ray diffraction pattern of amorphous Aramchol N-methylglucamine (meglumine) salt according to the present invention.

The present invention relates to unit dosage forms of salts of Aramchol which exhibit improved physicochemical properties including increased solubility, increased absorption, and increased exposure which correlates with higher bioavailability as compared with Aramchol free acid. Pharmaceutical compositions in unit dosage forms according to the invention advantageously comprise low doses of Aramchol amine salts. Thus, the compositions may provide surprisingly enhanced clinical properties, including therapeutic efficacy and/or reduced toxicity, or may be employed in improved and advantageous dosing regimens as disclosed herein.

According to the principles of the present invention, provided herein are pharmaceutically acceptable salts of Aramchol in which the counter ion is based on an amine and includes ammonia, a primary amine, a secondary amine, a tertiary amine, a quaternary ammonium compound, an amino alcohol, an amino sugar or an amino acid. The amine may also be a diamine or a cyclic amine. Currently preferred salts are N-methylglucamine (meglumine), lysine or tromethamine salts. Each possibility represents a separate embodiment of the present invention.

As used herein, the weight of Aramchol in the compositions of the invention is based on the weight of Aramchol free acid, and does not include the weight of the salt counterion, i.e., amino alcohols, amino sugars or amino acids.

As used herein, the term "primary amine" designates a compound of formula $R^aNH_2$ wherein $R^a$ is alkyl, cycloalkyl or aryl. Examples of primary amines are lower alkylamines wherein lower alkyl means a $C_1$-$C_4$ alkyl, or arylamines. The primary amine may react with the carboxylic acid group of Aramchol to form the salt Aramchol-$COO^-R^aNH_3^+$.

As used herein, the term "secondary amine" designates a compound of formula $R^aR^bNH$ wherein each of $R^a$ and $R^b$ is independently alkyl, cycloalkyl or aryl. Examples of secondary amines are lower dialkylamines ($R^a$, $R^b$ are each a lower alkyl), diarylamines, or alkylarylamines. The secondary amine may also be a cyclic amine (e.g., morpholine, pyrrolidine, piperidine, etc.), or a diamine (e.g., benzathaine). The secondary amine may react with the carboxylic acid group of Aramchol to form the salt Aramchol-$COO^-R^aR^bNH_2^+$.

As used herein, the term "tertiary amine" designates a compound of formula $R^aR^bR^cN$ wherein each of $R^a$, $R^b$ and $R^c$ is independently alkyl, cycloalkyl or aryl. Examples of tertiary amines are lower trialkylamines ($R^a$, $R^b$ and $R^c$ are each a lower alkyl), triarylamines, or any combination of alkylarylamines. The tertiary amine may also be a cyclic amine (e.g., N-methyl pyrrolidine, N-methylpiperidine, etc.) or a diamine. The tertiary amine may react with the carboxylic acid group of Aramchol to form the salt Aramchol-$COO^-\ R^aR^bR^cNH^+$.

As used herein, the term "quaternary ammonium compound" designates a compound of formula $R^aR^bR^cR^dN^+X^-$ wherein each of $R^a$, $R^b$, $R^c$ and $R^d$ is independently alkyl, cycloalkyl or aryl and $X^-$ is a counter-ion. Examples of quaternary ammonium compounds are lower tetraalkylamines ($R^a$, $R^b$, $R^c$ and $R^d$ are each a lower alkyl), tetraarylamines, or any combination of alkylarylamines. Specific examples of quaternary ammonium compounds which may form salts with Aramchol according to the present invention are $Bu_4N^+X^-$, choline ($Me_3N^+CH_2CH_2OH]X^-$) or trimethylglycine (($CH_3)_3N^+CH_2CO_2HX^-$, also known as betaine), wherein X is a counter-ion, for example OH, halogen (F, Cl, Br, I) and the like. The quaternary ammonium compound may react with the carboxylic acid group of Aramchol to form the salt Aramchol-$COO^-\ R^aR^bR^cR^dN^+$.

As used herein, the term "amino alcohol" or "alkanolamine", used herein interchangeably means compounds that contain both hydroxy (—OH) and amino (—$NH_2$, —NHR, and —$N(R)_2$) functional groups on an alkane backbone. Examples include but are not limited to tromethamine, ethanolamine, diethanolamine, 2-diethylaminoethanol and 2-dimethylaminoethanol.

As used herein, the term "amino sugar" or "amino sugar alcohol" means a sugar or sugar alcohol moiety in which one of the sugar hydroxyls has been replaced by an amino group. Examples of amino sugars are N-alkyl glucamines, for example N-methylglucamine (meglumine), N-ethylglucamine (eglumine), N-propylglucamine, N-butylglucamine and the like.

Thus, in some exemplary embodiments, the present invention provides unit dosage forms of salts of Aramchol with suitable organic amines such as, but not limited to, unsubstituted or substituted lower alkylamines, diamines, saturated cyclic amines, and quaternary ammonium compounds. Each possibility represents a separate embodiment of the present invention. Particular examples include, but are not limited to, methylamine, dimethylamine, trimethylamine, triethylamine, ethylamine, diethylamine, ethylenediamine, ethanolamine, diethanolamine, triethanolamine, tromethamine (TRIS), 1-amino-2-propanol, 3-amino-1-propanol, hexamethylenetetramine, deanol, 2-diethylaminoethanol, N-methylglucamine (meglumine), N-ethylglucamine (eglumine), piperidine, piperazine, pyrrolidine, morpholine, benzathine, trimethylglycine (betaine), choline and the like. Each possibility represents a separate embodiment of the present invention.

In some aspects and embodiments, the present invention provides unit dosage forms of the N-methylglucamine (meglumine) salt of Aramchol. In one embodiment, the N-methylglucamine salt of Aramchol is amorphous.

In further aspects and embodiments, the present invention provides unit dosage forms of the tromethamine (TRIS) salt of Aramchol. In one embodiment, the tromethamine salt of Aramchol is amorphous.

In further aspects and embodiments, the present invention provides unit dosage forms of the ammonium salt of Aramchol. In one embodiment, the ammonium salt of Aramchol is crystalline. In another embodiment, the ammonium salt of Aramchol is characterized by a DSC-TGA thermogram having a peak at about 76° C. with an onset at about 60° C. and a peak at about 117° C. with an onset at about 114° C. In specific embodiments, the peak at about 76° C. is accompanied by weight loss of about 2%. In yet another embodiment, the ammonium salt of Aramchol is characterized by a DSC-TGA thermogram having a peak at about 57° C. with an onset at about 55° C. In particular embodiments, the peak at about 57° C. is accompanied by weight loss of about 5%.

In other aspects and embodiments, the present invention provides unit dosage forms of the benzathine salt of Aramchol. In one embodiment, the benzathine salt of Aramchol is amorphous.

In further aspects and embodiments, the present invention provides unit dosage forms of the trimethylglycine (betaine) salt of Aramchol. In one embodiment, the trimethylglycine (betaine) salt of Aramchol is amorphous.

In yet other aspects and embodiments, the present invention provides unit dosage forms of the ethanolamine salt of Aramchol. In one embodiment, the ethanolamine salt of Aramchol is amorphous. In another embodiment, the ethanolamine salt of Aramchol is crystalline. In specific embodiments, the crystalline ethanolamine salt of Aramchol is characterized by a DSC-TGA thermogram having a peak at about 50° C. with an onset at about 45° C., a peak at about 72° C. with an onset at about 63° C., a peak at about 86° C. with an onset at about 80° C., and a peak at about 122° C.

with an onset at about 105° C. In particular embodiments, the peaks are characterized by a continuous weight loss of about 25%.

In certain aspects and embodiments, the present invention provides unit dosage forms of the diethanolamine salt of Aramchol. In one embodiment, the diethanolamine salt of Aramchol is amorphous.

In additional aspects and embodiments, the present invention provides unit dosage forms of the diethylamine salt of Aramchol. In one embodiment, the diethylamine salt of Aramchol is amorphous.

In other aspects and embodiments, the present invention provides unit dosage forms of the choline salt of Aramchol. In one embodiment, the choline salt of Aramchol is amorphous.

In yet other aspects and embodiments, the present invention provides unit dosage forms of the deanol salt of Aramchol. In one embodiment, the deanol salt of Aramchol is amorphous.

In several aspects and embodiments, the present invention provides unit dosage forms of the 2-diethylaminoethanol salt of Aramchol. In one embodiment, the 2-diethylaminoethanol salt of Aramchol is amorphous.

In some aspects and embodiments, the present invention provides unit dosage forms of the amino acids salts of Aramchol including, but not limited to basic amino acids such as lysine, arginine, histidine, and ornithine. Each possibility represents a separate embodiment of the present invention. The amino acids, according to the principles of the present invention, may be D-amino acids, L-amino acids, or racemic derivatives of amino acids. In one embodiment, the present invention provides the unit dosage forms of arginine salt of Aramchol. In another embodiment, the present invention provides unit dosage forms of the lysine salt of Aramchol. In some embodiments, the amino acids salts of Aramchol are other than the glycine and taurine salts of Aramchol. In certain embodiments, the amino acids salts of Aramchol are amorphous. A currently preferred amino acid salt of Aramchol is the lysine salt. In some embodiments, the lysine salt is amorphous.

It is understood that the pharmaceutically acceptable salts of the present invention, when isolated in solid or crystalline form, also include hydrates or water molecules entrapped therein.

It is to be understood that the conjugation between the fatty acid radical and the bile acid in Aramchol can be in the α or the β configuration. Each possibility represents a separate embodiment of the present invention. The Aramchol salts of the present invention can be amorphous or crystalline in any polymorphic form.

The novel salts of the present invention are useful as pharmaceuticals for medical treatment. The present invention thus provides unit dosage forms of pharmaceutical compositions comprising any of the Aramchol salts disclosed herein and at least one pharmaceutically acceptable carrier, diluent, vehicle or excipient. The unit dosage forms of the present invention can be safely administered orally or non-orally. Routes of administration include, but are not limited to, oral, topical, subcutaneous, intraperitoneal, rectal, intravenous, intra-arterial, transdermal, intramuscular, topical, and intranasal. Each possibility represents a separate embodiment of the present invention. Additional routes of administration include, but are not limited to, mucosal, nasal, parenteral, gastrointestinal, intraspinal, intrauterine, intraocular, intradermal, intracranial, intratracheal, intravaginal, intracerebroventricular, intracerebral, ophthalmic, buccal, epidural and sublingual. Each possibility represents a separate embodiment of the present invention. Typically, the unit dosage forms of the present invention are administered orally.

The unit dosage forms of the pharmaceutical compositions can be formulated as tablets (including e.g. film-coated tablets), powders, granules, capsules (including soft capsules), orally disintegrating tablets, pills, pellets, lozenges, sachets, cachets, patches, elixirs, suspensions, dispersions, emulsions, solutions, syrups, aerosols, ointments, soft and hard gelatin capsules, suppositories, sterile injectable solutions, sterile packaged powders, and sustained-release preparations as is well known in the art. Each possibility represents a separate embodiment of the present invention.

Pharmacologically acceptable carriers, diluents, vehicles or excipients that may be used in the context of the present invention include, but are not limited to, surfactants, lubricants, binders, fillers, compression aids, disintegrants, water-soluble polymers, inorganic salts, preservatives, antioxidants, coloring agents, sweetening agents, souring agents, bubbling agents and flavorings. Each possibility represents a separate embodiment of the present invention.

Specific non-limiting examples of suitable carriers, diluents, vehicles or excipients include e.g. lactose, D-mannitol, starch, cornstarch, crystalline cellulose, light silicic anhydride and titanium oxide. Each possibility represents a separate embodiment of the present invention. Suitable surfactants include e.g. lecithin and phosphatidylcholine. Each possibility represents a separate embodiment of the present invention. Suitable lubricants include e.g. magnesium stearate, sucrose fatty acid esters, polyethylene glycol, talc and stearic acid. Each possibility represents a separate embodiment of the present invention. Suitable binders include e.g. hydroxypropyl cellulose, hydroxypropylmethyl cellulose, crystalline cellulose, α-starch, polyvinylpyrrolidone, gum arabic powder, gelatin, pullulan and low-substitutional hydroxypropyl cellulose. Each possibility represents a separate embodiment of the present invention. Suitable disintegrants include e.g. crosslinked povidone (any crosslinked 1-ethenyl-2-pyrrolidinone homopolymer including polyvinylpyrrolidone (PVPP) and 1-vinyl-2-pyrrolidinone homopolymer), crosslinked carmellose sodium, carmellose calcium, carboxymethyl starch sodium, low-substituted hydroxypropyl cellulose, cornstarch and the like. Each possibility represents a separate embodiment of the present invention. Suitable water-soluble polymers include e.g. cellulose derivatives such as hydroxypropyl cellulose, polyvinylpyrrolidone, hydroxypropylmethyl cellulose, methyl cellulose and carboxymethyl cellulose sodium, sodium polyacrylate, polyvinyl alcohol, sodium alginate, guar gum, and the like. Each possibility represents a separate embodiment of the present invention. Suitable inorganic salts include e.g. basic inorganic salts of sodium, potassium, magnesium and/or calcium. Each possibility represents a separate embodiment of the present invention. Particular embodiments include the basic inorganic salts of magnesium and/or calcium. Basic inorganic salts of sodium include, for example, sodium carbonate, sodium hydrogen carbonate, disodiumhydrogenphosphate, and the like. Each possibility represents a separate embodiment of the present invention. Basic inorganic salts of potassium include, for example, potassium carbonate, potassium hydrogen carbonate, and the like. Each possibility represents a separate embodiment of the present invention. Basic inorganic salts of magnesium include, for example, heavy magnesium carbonate, magnesium carbonate, magnesium oxide, magnesium hydroxide, magnesium metasilicate aluminate, magnesium silicate, magnesium aluminate, synthetic hydrotalcite, aluminahydroxidemagnesium, and the like. Each possibility represents a separate embodiment of the present invention. Basic inorganic salts of calcium include, for example, precipitated calcium carbonate, calcium hydroxide, and the like. Each possibility represents a separate embodiment of the present invention.

Suitable preservatives include e.g. sodium benzoate, benzoic acid, and sorbic acid. Each possibility represents a separate embodiment of the present invention. Suitable antioxidants include e.g. sulfites, ascorbic acid and α-tocopherol. Each possibility represents a separate embodiment of the present invention. Suitable coloring agents include e.g. food colors such as Food Color Yellow No. 5, Food Color Red No. 2 and Food Color Blue No. 2, and the like. Each possibility represents a separate embodiment of the present invention. Suitable sweetening agents include e.g. dipotassium glycyrrhetinate, aspartame, stevia and thaumatin. Each possibility represents a separate embodiment of the present invention. Suitable souring agents include e.g. citric acid (citric anhydride), tartaric acid and malic acid. Each possibility represents a separate embodiment of the present invention. Suitable bubbling agents include e.g. sodium bicarbonate. Suitable flavorings include synthetic substances or naturally occurring substances, including e.g. lemon, lime, orange, menthol and strawberry. Each possibility represents a separate embodiment of the present invention.

In some embodiments, the present invention provides a unit dosage form of a pharmaceutical composition comprising as an active ingredient a single Aramchol salt of the present invention and at least one pharmaceutically acceptable carrier, diluent, vehicle or excipient. In other embodiments, the present invention provides a unit dosage forms of a pharmaceutical composition comprising as an active ingredient a plurality of Aramchol salts of the present invention and at least one pharmaceutically acceptable carrier, diluent, vehicle or excipient.

The unit dosage forms of the present invention are particularly suitable for oral administration in the form of tablets, capsules, pills, dragees, powders, granules and the like. Each possibility represents a separate embodiment of the present invention. A tablet may be made by compression or molding, optionally with one or more excipients as is known in the art. Specifically, molded tablets may be made by molding in a suitable machine a mixture of the powdered active ingredient moistened with an inert liquid diluent.

The tablets and other solid dosage forms of the pharmaceutical compositions described herein may optionally be scored or prepared with coatings and shells, such as enteric coatings and other coatings well known in the art. They may also be formulated so as to provide slow or controlled release of the active ingredient therein using, for example, hydroxypropylmethyl cellulose in varying proportions to provide the desired release profile, other polymer matrices and the like. The active ingredient can also be in microencapsulated form, if appropriate, with one or more of the above-described excipients.

The present invention provides a method of reducing cholesterol levels in the blood or treating fatty liver comprising administering to a subject in need thereof a therapeutically effective amount of a unit dosage form of a composition comprising any one of the Aramchol salts of the present invention. The present invention provides a method of treating fatty liver disease and non-alcoholic SteatoHepatitis (NASH) comprising administering to a subject in need thereof a unit dosage form of a therapeutically effective amount of a composition comprising any one of the Aramchol salts of the present invention. The present invention further provides a method of dissolving cholesterol gallstones in bile and/or for preventing formation of such gallstones comprising administering to a subject in need thereof a unit dosage form of a therapeutically effective amount of a composition comprising any one of the Aramchol salts of the present invention. In other embodiments, the present invention provides a method of treating arteriosclerosis comprising administering to a subject in need thereof a unit dosage form of a therapeutically effective amount of a composition comprising any one of the Aramchol salts of the present invention. The present invention also provides a method of treating a disease or disorder associated with altered glucose metabolism, particularly hyperglycemia, diabetes, insulin resistance and obesity, comprising administering to a subject in need thereof a unit dosage form of a therapeutically effective amount of a composition comprising any one of the Aramchol salts of the present invention. The present invention further provides a method of treating, preventing, or inhibiting progression of a brain disease characterized by amyloid plaque deposits, particularly Alzheimer's disease, comprising administering to a subject in need thereof a unit dosage form of a therapeutically effective amount of a composition comprising any one of the Aramchol salts of the present invention.

A "therapeutically effective amount" as used herein refers to an amount of an agent which is effective, upon single or multiple dose administration to the subject in providing a therapeutic benefit to the subject. In additional embodiments, the Aramchol salts of the present invention are used for the preparation of a medicament for treating the aforementioned diseases or disorders. Thus, as detailed herein, a therapeutically effective amount of an amine salt of the invention may include low doses, not hitherto considered to exert adequate or sufficient therapeutic benefit in a given disease or condition. Therefore, the dosages or amounts considered by the present invention to be therapeutically effective may not be considered as such by prior disclosures of the inventors of the present invention, or by persons of skill in the art of Aramchol therapy.

Throughout the present invention, and unless otherwise specifically indicated, the therapeutically effective amount is defined by the amount of the active ingredient, namely the 3β-arachidylamido-7α,12α-dihydroxy-5β-cholan-24-oic acid (Aramchol) component (Aramchol carboxylate) of the Aramchol/amine salt, as detailed herein, based on the weight of Aramchol free acid.

The improved clinical properties of the dosage forms of Aramchol amine salts of the present invention further provide for two marked benefits from a clinical point of view, namely the ability to administer medium-dose Aramchol when high-dose Aramchol is usually required to achieve a favorable clinical outcome, and the ability to administer low-dose Aramchol when medium-dose Aramchol is usually required to achieve a favorable clinical outcome. For example, U.S. Pat. No. 8,975,246 studied the effects of 100 and 300 mg Aramchol daily on 60 human patients. Aramchol, particularly when given at a dose of 300 mg per day, was described to increase the levels of adiponectin (a hormone associated with inhibition of insulin resistance) and reduce glucose and basal insulin levels. The novel amine salts described herein may be used in the methods of the invention to provide enhanced efficacy even at lower doses than those hitherto considered to be required to produce enhanced efficacy.

In certain embodiments, a therapeutically effective amount of an Aramchol amine salt is significantly lower than the therapeutically effective amount of Aramchol as free acid. In certain embodiments, a therapeutically effective amount of an Aramchol amine salt is at least 25% by weight lower than a therapeutically effective amount of Aramchol as free acid. In certain advantageous embodiments, a therapeutically effective amount of an Aramchol amine salt is at least 30%, at least 40%, at least 50%, at least 60% or at least 70% by weight lower than a therapeutically effective amount of Aramchol as free acid. In certain embodiments, a therapeutically effective amount of an Aramchol amine salt is at least 75% by weight lower than a therapeutically effective amount of Aramchol as free acid.

Thus, according to embodiments of the invention, the compositions of the invention comprise a therapeutically effective amount of an Aramchol salt corresponding to a dose within the range of about 10 to 400 mg of the free Aramchol acid (molar equivalent thereof).

As used herein, the term "about," when referring to a value or to an amount of mass, weight, time, volume, concentration or percentage is meant to encompass variations, as such variations are appropriate to perform the disclosed method as determined by the skilled artisan. The term encompasses variations of up to ±20% and typically no more than ±10%. For example, in some embodiments, the variations may be of ±5%, ±1%, ±0.5%, or ±0.1% from the specified amount, as such variations are appropriate to perform the disclosed method.

Thus, the invention relates in various embodiments to pharmaceutical compositions in unit dosage form comprising a therapeutically effective amount of a salt comprising a 3β-arachidylamido-7α,12α-dihydroxy-5β-cholan-24-oic acid (Aramchol) anion and a protonated amine cation, in which the Aramchol anion is present in an amount of 10 to 400 mg; and optionally at least one pharmaceutically acceptable carrier, diluent, vehicle or excipient. According to exemplary embodiments, the amount of the Aramchol anion in said compositions is selected from the group consisting of (i) 10 to 25 mg; (ii) 10 to 100 mg; (iii) 30 to 100 mg; (iv) 30 to 200 mg; (v) 100 to 200 mg; (vi) 30 to 300 mg; (vii) 100 to 300 mg; and (viii) 200 to 300 mg.

The corresponding equivalent dose may be readily determined based on the molecular weight of each salt, in comparison to that of free Aramchol free acid (702.1). For instance, the molecular weight of exemplary amine salts of Aramchol with an L-Lysine, Tromethamine or N-Me-Glucamine base is 848.3, 823.2 and 897.3, respectively. Accordingly, the respective weight percent of the Aramchol active ingredient in these salts is 83%, 85% and 78%. Thus, for example, the total doses of these salts (including the amine counterion) that are equivalent to 100 mg free Aramchol are 120.5, 117.6 and 128.2, respectively.

In certain embodiments, the therapeutically effective amount of the amine salt of 3β-arachidylamido-7α,12α-dihydroxy-5β-cholan-24-oic acid may be administered daily in two or more administrations. In certain embodiments, the therapeutically effective amount of the amine salt of 3β-arachidylamido-7α,12α-dihydroxy-5β-cholan-24-oic acid may be administered daily in 2, 3, 4 or 5 separate administrations per day. Each possibility represents a separate embodiment of the invention. In other certain embodiments, the therapeutically effective amount of the amine salt of 3β-arachidylamido-7α,12α-dihydroxy-5β-cholan-24-oic acid may be administered weekly or monthly in one, two or more administrations. In certain embodiments, the therapeutically effective amount of the amine salt of 3β-arachidylamido-7α,12α-dihydroxy-5β-cholan-24-oic acid may be administered daily in 2, 3, 4 or 5 separate administrations per week. In certain embodiments, the therapeutically effective amount of the amine salt of 3β-arachidylamido-7α,12α-dihydroxy-5β-cholan-24-oic acid may be administered daily in 2, 3, 4 or 5 separate administrations per month. Each possibility represents a separate embodiment of the invention.

The composition may be administered to said subject according to certain embodiments of the invention in a dosage regimen selected from the group consisting of: (i) once a day; (ii) 2 to 4 separate administrations per day; (iii) 2 to 4 separate administrations per week; and (iv) 2 to 4 separate administrations per month. In another embodiment a therapeutically effective amount of the salt in which the Aramchol component is present in an amount of 200 to 300 mg is administered daily to said subject. In a particular embodiment a therapeutically effective amount of the salt in which the Aramchol component is present in an amount of about 260 mg is administered daily to said subject. In another embodiment a therapeutically effective amount of the salt in which the Aramchol component is present in an amount of 300 to 400 mg is administered daily to said subject. In yet another particular embodiment a therapeutically effective amount of the salt in which the Aramchol component is present in an amount of about 400 mg is administered daily to said subject.

In certain other embodiments of the methods of the present invention, a treatment regimen of an Aramchol amine salt may include daily administration (in one or more doses) of 300 mg or more, e.g. 350, 400 or 450 mg of the active ingredient. In certain embodiments, these dosages are significantly lower than the equivalent therapeutically effective amount of Aramchol as free acid.

In other certain embodiments of the methods of the present invention, unit dosage forms comprising an Aramchol amine salt of the invention in doses lower than 30, 25 or 10 mg of the active ingredient, are administered to the subject in the course of the treatment regimen (once a day or multiple times a day). For example, the use of doses of 1 to 9 mg, e.g. 1, 2, 3, 4, 5, 6, 7, 8 or 9 mg, may be contemplated. In yet other embodiments, doses of about 25-50, 25-90, 40-90 or 40-150 mg may be used. In certain embodiments, these dosages are significantly lower than the equivalent therapeutically effective amount of Aramchol as free acid.

In another aspect, there is provided a pharmaceutical composition in unit dosage form comprising a therapeutically effective amount of a salt of 3β-arachidylamido-7α, 12α-dihydroxy-5β-cholan-24-oic acid (Aramchol) with an amine, in which the Aramchol component is present in an amount of 10 to 400 mg based on the weight of Aramchol free acid; and optionally at least one pharmaceutically acceptable carrier, diluent, vehicle or excipient, for use in the treatment of a disease or condition amenable for treatment by Aramchol in a human subject in need thereof.

In some embodiments, the disease or condition is selected from the group consisting of conditions associated with fatty liver, high cholesterol levels in the blood, altered glucose metabolism, gallstones, amyloid plaque deposits and arteriosclerosis. In other embodiments, the amount of said Aramchol component is selected from the group consisting of (i) 10 to 25 mg; (ii) 10 to 100 mg; (iii) 30 to 100 mg; (iv) 30 to 200 mg; (v) 100 to 200 mg; (vi) 30 to 300 mg; (vii) 100 to 300 mg; and (viii) 200 to 300 mg. In another embodiment the amine is selected from the group consisting of ammonia, a primary amine, a secondary amine, a tertiary amine, a quaternary ammonium compound, an amino alcohol, an amino sugar and an amino acid. In another embodiment the amine is selected from the group consisting of an amino alcohol, an amino sugar and an amino acid. In another embodiment the salt is selected from the group consisting of ammonium, benzathine, trimethylglycine (betaine), ethanolamine, diethanolamine, diethylamine, arginine, lysine, choline, deanol, 2-diethylaminoethanol, N-methylglucamine (meglumine), N-ethylglucamine (eglumine), and tromethamine salts. In a particular embodiment, said composition comprises 3β-arachidylamido-7α,12α-dihydroxy-5β-cholan-24-oic acid lysine salt. In another particular embodiment, said composition comprises 3β-arachidylamido-7α,12α-dihydroxy-5β-cholan-24-oic acid tromethamine salt. In another particular embodiment, said composition comprises 3β-arachidylamido-7α,12α-dihydroxy-5β-cholan-24-oic acid N-methylglucamine salt. In another embodiment the salt is in a crystalline form. In another embodiment the salt is in an amorphous form. In another embodiment the ratio between the 3β-arachidylamido-7α,12α-dihydroxy-5β-cholan-24-oic acid and the amine is about 1:1. In another embodiment said composition is in a form suitable for oral administration to a human subject. In another embodiment said composition is formulated in solid oral dosage form. In another embodiment said composition is formulated in a form selected from the group consisting of tablets, pills, capsules, pellets, granules, powders, lozenges, sachets, cachets, patches, elixirs, suspensions, dispersions, emulsions, solutions, syrups, aerosols, ointments, soft and hard gelatin capsules, suppositories, sterile injectable solutions, and sterile packaged powders. Each possibility represents a separate embodiment of the invention.

In another aspect, the invention is directed to the use of a pharmaceutical composition in unit dosage form comprising a therapeutically effective amount of a salt of 3β-arachidylamido-7α,12α-dihydroxy-5β-cholan-24-oic acid (Aramchol) with an amine, in which the Aramchol component is present in an amount of 10 to 400 mg based on the weight of Aramchol free acid; and optionally at least one pharmaceutically acceptable carrier, diluent, vehicle or excipient, for the preparation of a medicament for use in the treatment of a disease or condition amenable for treatment by Aramchol in a human subject in need thereof.

In some embodiments, the disease or condition is selected from the group consisting of conditions associated with fatty liver, high cholesterol levels in the blood, altered glucose metabolism, gallstones, amyloid plaque deposits and arteriosclerosis. In other embodiments, the amount of said Aramchol component is selected from the group consisting of (i) 10 to 25 mg; (ii) 10 to 100 mg; (iii) 30 to 100 mg; (iv) 30 to 200 mg; (v) 100 to 200 mg; (vi) 30 to 300 mg; (vii) 100 to 300 mg; and (viii) 200 to 300 mg. In another embodiment the amine is selected from the group consisting of ammonia, a primary amine, a secondary amine, a tertiary amine, a quaternary ammonium compound, an amino alcohol, an amino sugar and an amino acid. In another embodiment the amine is selected from the group consisting of an amino alcohol, an amino sugar and an amino acid. In another embodiment the salt is selected from the group consisting of ammonium, benzathine, trimethylglycine (betaine), ethanolamine, diethanolamine, diethylamine, arginine, lysine, choline, deanol, 2-diethylaminoethanol, N-methylglucamine (meglumine), N-ethylglucamine (eglumine), and tromethamine salts. In a particular embodiment, said composition comprises 3β-arachidylamido-7α,12α-dihydroxy-5β-cholan-24-oic acid lysine salt. In another particular embodiment, said composition comprises 3β-arachidylamido-7α,12α-dihydroxy-5β-cholan-24-oic acid tromethamine salt. In another particular embodiment, said composition comprises 3β-arachidylamido-7α,12α-dihydroxy-5β-cholan-24-oic acid N-methylglucamine salt. In another embodiment the salt is in a crystalline form. In another embodiment the salt is in an amorphous form. In another embodiment the ratio between the 3β-arachidylamido-7α,12α-dihydroxy-5β-cholan-24-oic acid and the amine is about 1:1. In another embodiment said composition is in a form suitable for oral administration to a human subject. In another embodiment said composition is formulated in solid oral dosage form. In another embodiment said composition is formulated in a form selected from the group consisting of tablets, pills, capsules, pellets, granules, powders, lozenges, sachets, cachets, patches, elixirs, suspensions, dispersions, emulsions, solutions, syrups, aerosols, ointments, soft and hard gelatin capsules, suppositories, sterile injectable solutions, and sterile packaged powders. Each possibility represents a separate embodiment of the invention.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1—Synthesis of Aramchol Salts

The Aramchol salts of the present invention were prepared according to the following procedure: Aramchol free acid was mixed with the corresponding base in a ratio of 1:1 in water or ethanol. The mixture was heated to 50° C. at a rate of 1° C./min. The mixture was kept at 50° C. for 2 hours, and cooled at a rate of 0.1° C./min to 20° C. in cases where the salts did not precipitate out after cooling, the crude reaction mixtures were maintained for 3 days and the purity was measured by HPLC. The Aramchol salts which provided a clear solution showed no additional impurities on HPLC. The results are summarized in Table 1.

The following Aramchol salts were found to be soluble (>50 mg/ml at 50° C.) in water: L-arginine salt, choline salt, N-methylglucamine salt, diethylamine salt, 2-diethylaminoethanol salt, deanol salt, ethanolamine salt, and diethanolamine salt. The following Aramchol salts were found to be soluble (>50 mg/ml at 50° C.) in ethanol at 50° C.: L-arginine salt, choline salt, trimethylglycine (betaine) salt, diethylamine salt, benzathine salt, 2-diethylamino-ethanol salt, deanol salt, tromethamine salt, and diethanolamine salt. No salts were obtained using glycine or taurine.

Using water as a solvent, the following Aramchol salts precipitated as amorphous material: L-arginine salt, L-lysine salt, choline salt, N-methylglucamine salt, diethylamine salt, benzathine salt, 2-diethylamino-ethanol salt, deanol salt, ethanolamine salt, and diethanolamine salt. A crystalline ammonium salt of Aramchol was obtained from water (Form I). The form was characterized by thermal analysis. The DSC profile showed a first peak at 76.32° C. with an onset at 60.07° C. (ΔE=−29.33 J/g) and a second peak at 117.12° C. with an onset at 114.08° C. (ΔE=−67.16 J/g). The weight loss during the first peak was 2.05%.

TABLE 1

| Base | Dissolved (50 mg/ml) at 50° C. | XRPD | salt remains in solution after cooling to 20° C. | Stability in water (HPLC) after 3 days |
|---|---|---|---|---|
| L-Arginine | Yes | n.a. | no | — |
| L-Lysine | No | Starting material | — | — |
| Choline | Yes | n.a. | yes | good |
| Ammonia | No | crystalline | no | — |
| N-methyl-glucamine | Yes | n.a. | no | — |
| Trimethyl-glycine (betaine) | No | Starting material | — | — |
| Diethylamine | Yes | n.a. | no | — |
| Benzathine | No | Amorphous | — | — |
| 2-diethylamino-ethanol | Yes | n.a. | yes | good |
| Deanol | Yes | n.a. | yes | good |
| Tromethamine | No | Starting material | — | — |
| Ethanolamine | Yes | n.a. | no | — |
| Diethanolamine | Yes | n.a. | yes | good | n.a. = not available

Using ethanol as a solvent, the following Aramchol salts precipitated as amorphous material: L-arginine salt, choline salt, trimethylglycine (betaine) salt, diethylamine salt, benzathine salt, 2-diethylamino-ethanol salt, deanol salt, tromethamine salt, and diethanolamine salt. A crystalline ammonium salt of Aramchol was obtained from ethanol. The form was characterized by thermal analysis. The DSC profile showed a peak at 56.57° C. with an onset at 55.37° C. (ΔE:=−45.57 J/g). The weight loss during the peak was 5.44%. A crystalline ethanolamine salt of Aramchol was obtained from ethanol. The form was characterized by thermal analysis. The DSC profile showed a first peak at 50.12° C. with an onset at 44.87° C. (ΔE=−8.45 J/g); a second peak at 72.27° C. with an onset at 62.58° C. (ΔE=6.28 J/g); a third peak at 85.86° C. with an onset at 80.06° C. (ΔE=−6.20 J/g); and a fourth peak at 122.42° C. with an onset at 104.82° C. (ΔE=−45.78 J/g). A continuous weight loss of 25.37% was observed using TGA.

Example 2—Solubility of Aramchol Salts

The Aramchol salts of the present invention were further assessed for their solubility in water. The aqueous solubility was tested at 20° C. using the shake-flask method. 5 mg of each salt was weighed. Water was added stepwise until a clear solution was obtained (Table 2, solubility in water). The pH of each solution was measured (Table 2, pH after solubility). The results are summarized in Table 2.

TABLE 2

| Base | XRPD | Solubility in water (mg/ml) | pH of solution |
|---|---|---|---|
| L-Arginine | Amorphous | <11 | n.a. |
| L-Lysine | Amorphous | 10-32 | 8 |
| L-Lysine | Crystalline | 11-35 | 8 |
| Ammonia | Crystalline | <11 | n.a. |
| N-methyl glucamine | Amorphous | 113-1130 | 7 |
| Betaine | Amorphous | <11 | n.a. |
| Betaine | Crystalline | <11 | n.a. |
| Diethylamine | Amorphous | <11 | n.a. |
| Diethylamine | Crystalline | <11 | n.a. |
| Tromethamine | Poorly crystalline | <11 | n.a. |
| Tromethamine | Crystalline | 32-95 | 8 |
| Ethanolamine | Crystalline | <11 | n.a. |
| Diethanolamine | Crystalline | <11 | n.a. | n.a. = not available

In comparison, Aramchol (free acid) has limited solubility in aqueous media (solubility in buffer at pH 6.0<0.001 mg/mL, max solubility of 0.66 mg/ml in FeSSIF, pH=5).

Example 3—Synthesis and Characterization of Aramchol N-Methyl Glucamine, Tromethamine and Lysine Salts The synthesis of the N-methylglucamine, tromethamine and lysine salts of Aramchol was accomplished in accordance with General Methods 1 and 2.

General Method 1: An aqueous or alcoholic solution (e.g., methanol, ethanol) of Aramchol and ~1 molar equivalent of the desired base were heated (e.g., to reflux) until a homogenous solution formed, followed by the addition of an anti-solvent (such as ethyl acetate or acetone) to afford a suspension. The reaction mixture was optionally cooled. The formed salts were isolated by filtration, washed and dried.

Aramchol N-methylglucamine salt was prepared by General Method 1. Aramchol free acid (5.0 g) was mixed with 1.4 g (1 molar equivalent) of N-methylglucamine in water, methanol or ethanol, heated to reflux, followed by adding acetone or ethyl acetate as an anti-solvent, and cooling. A precipitate formed which was isolated and characterized as amorphous Aramchol N-methylglucamine salt. Similar procedures were performed using 1-20 g Aramchol and 1 molar equivalent of N-methylglucamine.

Aramchol lysine salt was prepared by General Method 1. Aramchol free acid (5.0 g) was mixed with 1.0 g (1 molar equivalent) of lysine in methanol or ethanol, heated to reflux, followed by adding acetone or ethyl acetate as an anti-solvent, and cooling. A precipitate formed which was isolated and characterized as amorphous Aramchol lysine salt. Similar procedures were performed using 1-20 g Aramchol and 1 molar equivalent of lysine.

Aramchol tromethamine salt was prepared by General Method 1. Aramchol free acid (5.0 g) was mixed with 0.9 g (1 molar equivalent) of tromethamine in methanol or ethanol, heated to reflux, followed by adding acetone or ethyl acetate as an anti-solvent, and cooling. A precipitate formed which was isolated and characterized as amorphous Aramchol tromethamine salt. Similar procedures were performed using 1-20 g Aramchol and 1 molar equivalent of tromethamine.

General Method 2: An aqueous or alcoholic solution of Aramchol and ~1 molar equivalent of the desired base were heated (e.g., to reflux) until a homogenous solution formed. The reaction was optionally cooled. The solvent was then removed (e.g., by rotovap under reduced pressure) to afford a solid which was isolated and dried.

Aramchol N-methylglucamine salt was prepared by General Method 2. Aramchol free acid (150.0 g) was mixed with N-methylglucamine (41.7 g) in methanol, and heated to reflux to obtain a homogenous solution. The solution was concentrated on rotovap at 50° C. to obtain a solid, which was characterized as amorphous Aramchol N-methylglucamine salt.

Aramchol lysine salt was prepared by General Method 2. Aramchol free acid (50.0 g) was mixed with lysine (10.4 g) in methanol, and heated to reflux to obtain a homogenous solution. The solution was concentrated on rotovap at 50° C. to obtain a solid, which was characterized as amorphous Aramchol lysine salt.

Aramchol tromethamine salt was prepared by General Method 2. Aramchol free acid (50.0 g) was mixed with tromethamine (8.6 g) in methanol, and heated to reflux to obtain a homogenous solution. The solution was concentrated on rotovap at 50° C. to obtain a solid, which was characterized as amorphous Aramchol tromethamine salt.

Characterization:

The X-ray powder diffraction (XRPD) studies were performed using a Bruker AXS D2 PHASER in Bragg-Brentano configuration, equipment #1549. Using a Cu anode at 30 kV, 10 mA; sample stage standard rotating; monochromatisation by a κβ-filter (0.5% Ni). Slits: fixed divergence slits 1.0 mm (=0.61°), primary axial Soller slit 2.5°, secondary axial Soller slit 2.5°. Detector: Linear detector LYNXEYE with receiving slit 5° detector opening. The standard sample holder (0.1 mm cavity in (510) silicon wafer) had a minimal contribution to the background signal.

Measurements conditions: scan range 5-45° 2θ, sample rotation 5 rpm, 0.5 s/step, 0.010°/step, 3.0 mm detector slit; and all measuring condition were logged in the instrument control file. As system suitability, corundum sample (NIST standard) was measured daily.

The software used for data collection is Diffrac.Commander v3.3.35. Data analysis was performed using Diffrac.Eva v 3.0. No background correction or smoothing was applied to the patterns. The contribution of the Cu-Kα$_2$ was stripped off using the Diffrac.Eva software.

Figure 2:
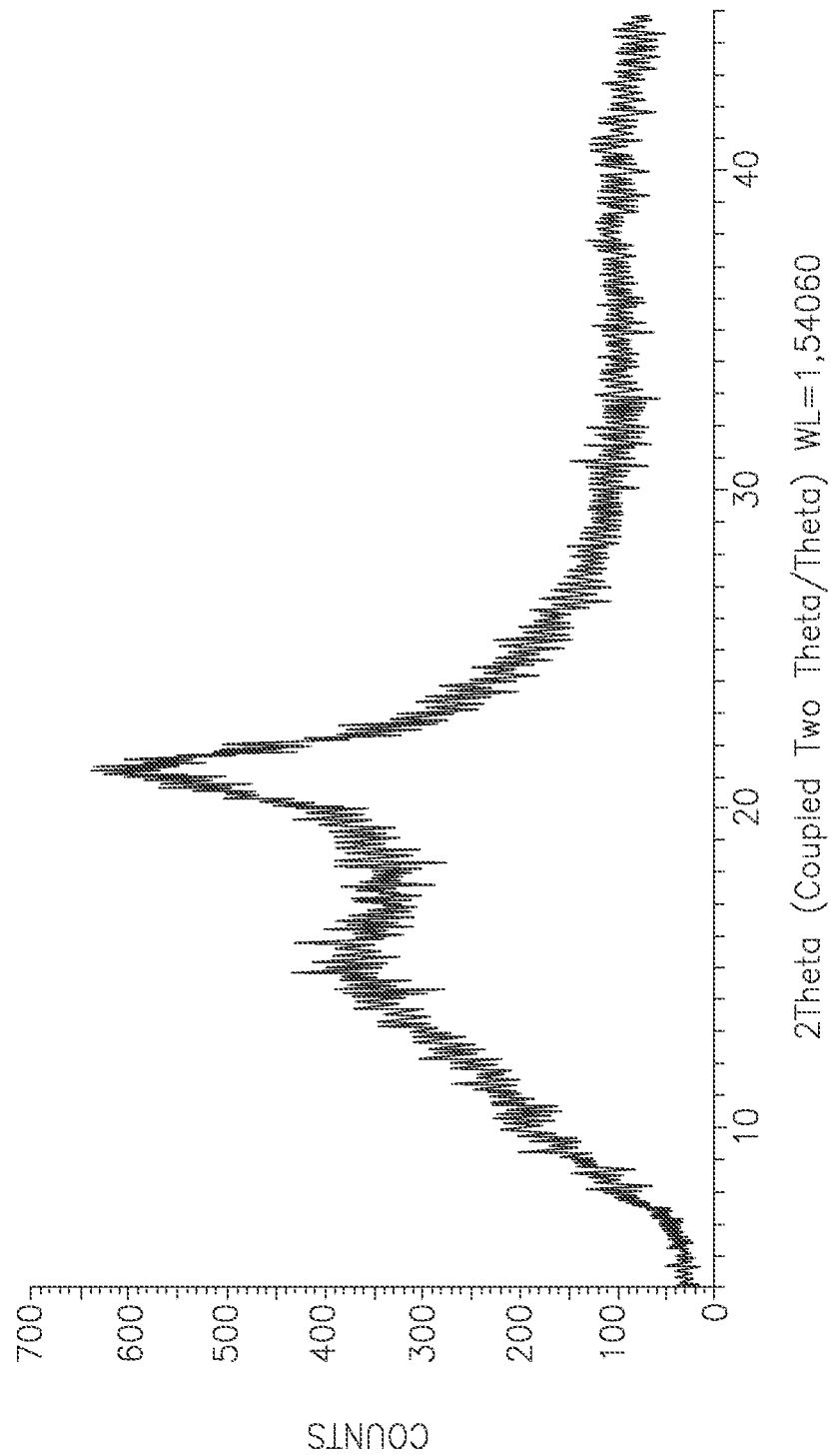
FIG. 2 illustrates a characteristic X-ray diffraction pattern of amorphous Aramchol lysine salt according to the present invention.
Figure 3:
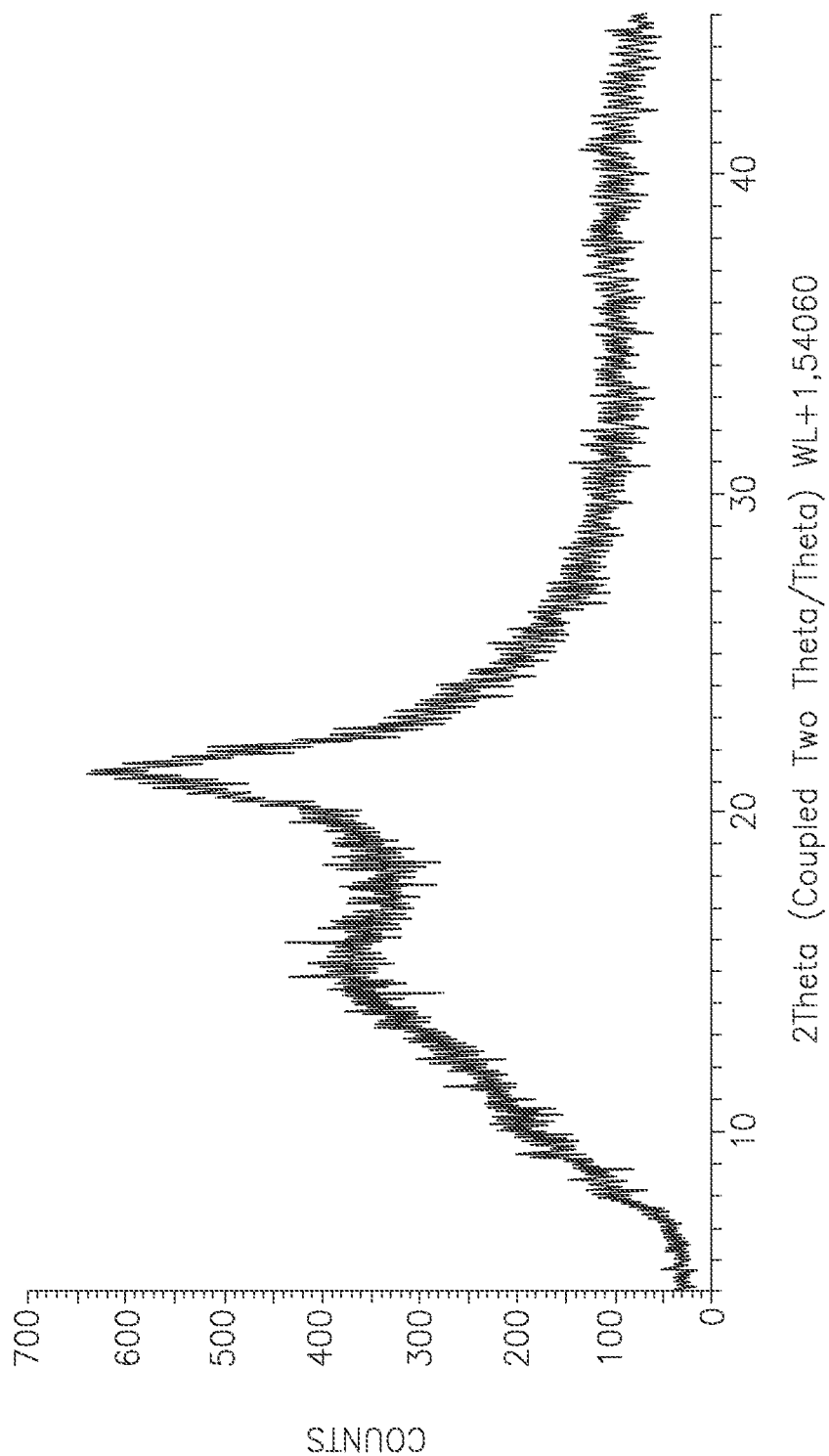
FIG. 3 illustrates a characteristic X-ray diffraction pattern of amorphous Aramchol tromethamine salt according to the present invention.

The XRPD analyses demonstrated that the resulting salts are amorphous. A representative XRPD spectrum of Aramchol N-methylglucamine salt is shown in FIG. 1. A representative XRPD spectrum of Aramchol lysine salt is shown in FIG. 2. A representative XRPD spectrum of Aramchol tromethamine salt is shown in FIG. 3.

Figure 4:
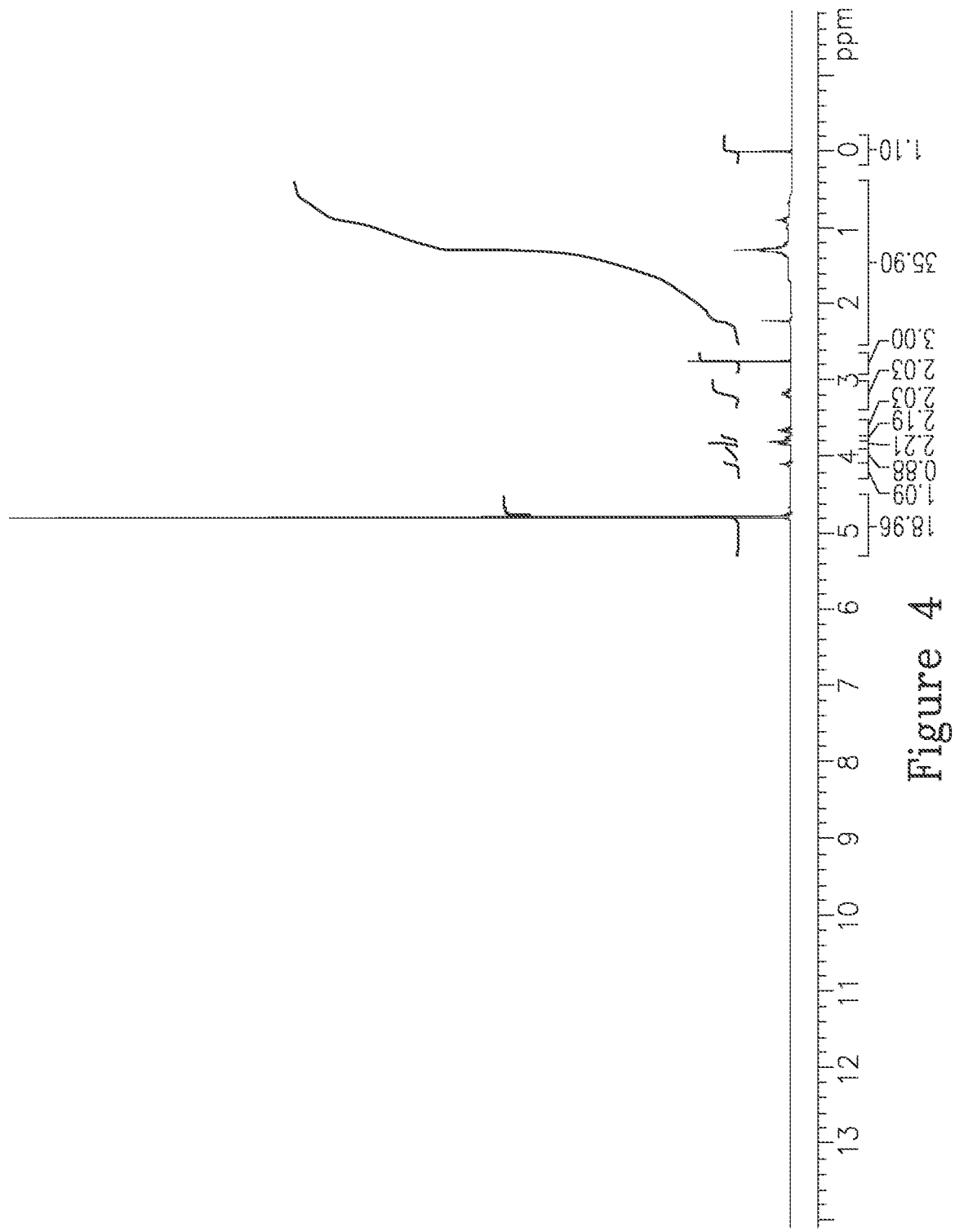
FIG. 4 illustrates a characteristic $^1$H-NMR spectrum of Aramchol N-methylglucamine salt according to the present invention.
Figure 5:
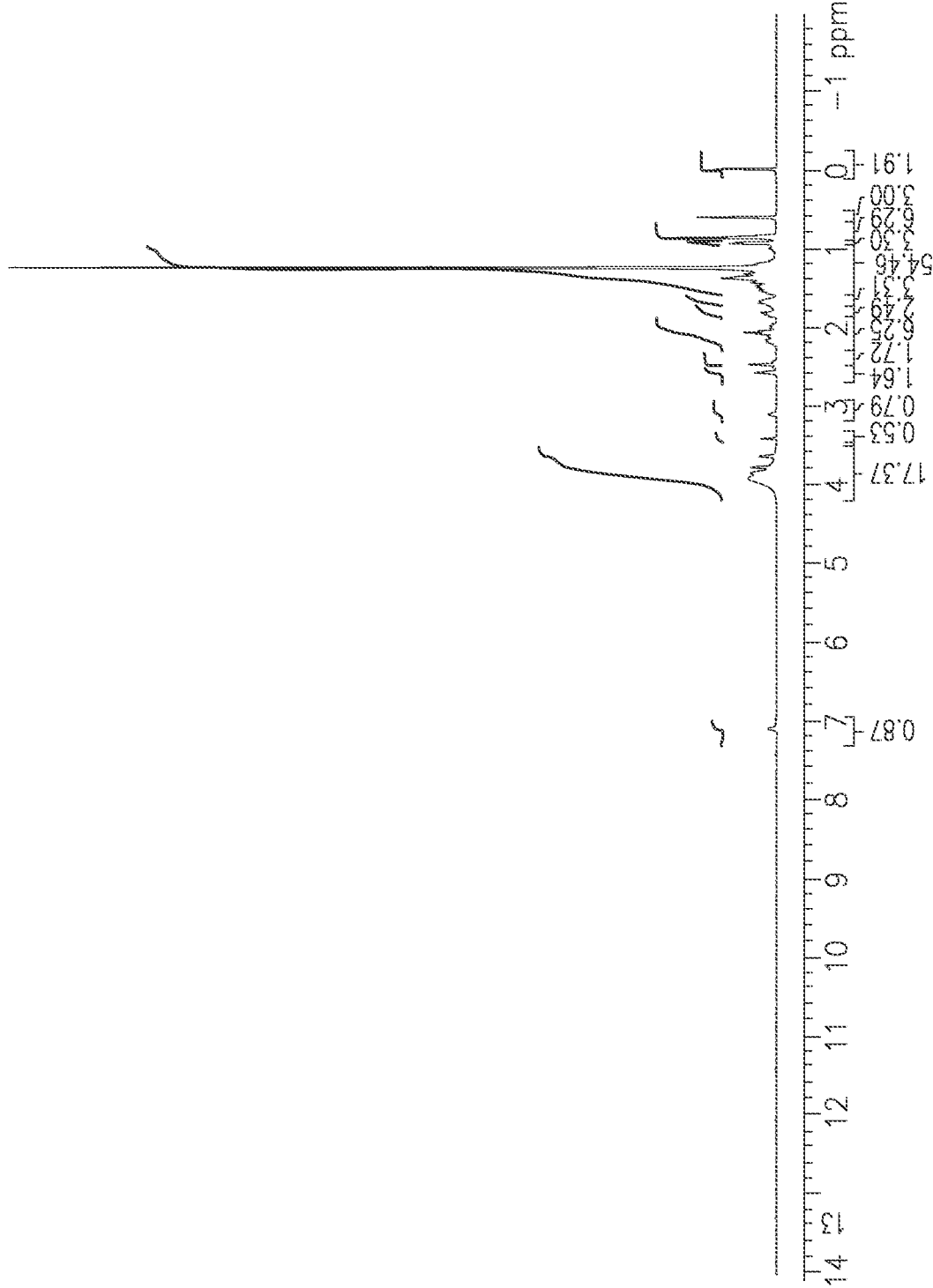
FIG. 5 illustrates a characteristic $^1$H-NMR spectrum of Aramchol lysine salt according to the present invention.
Figure 6:
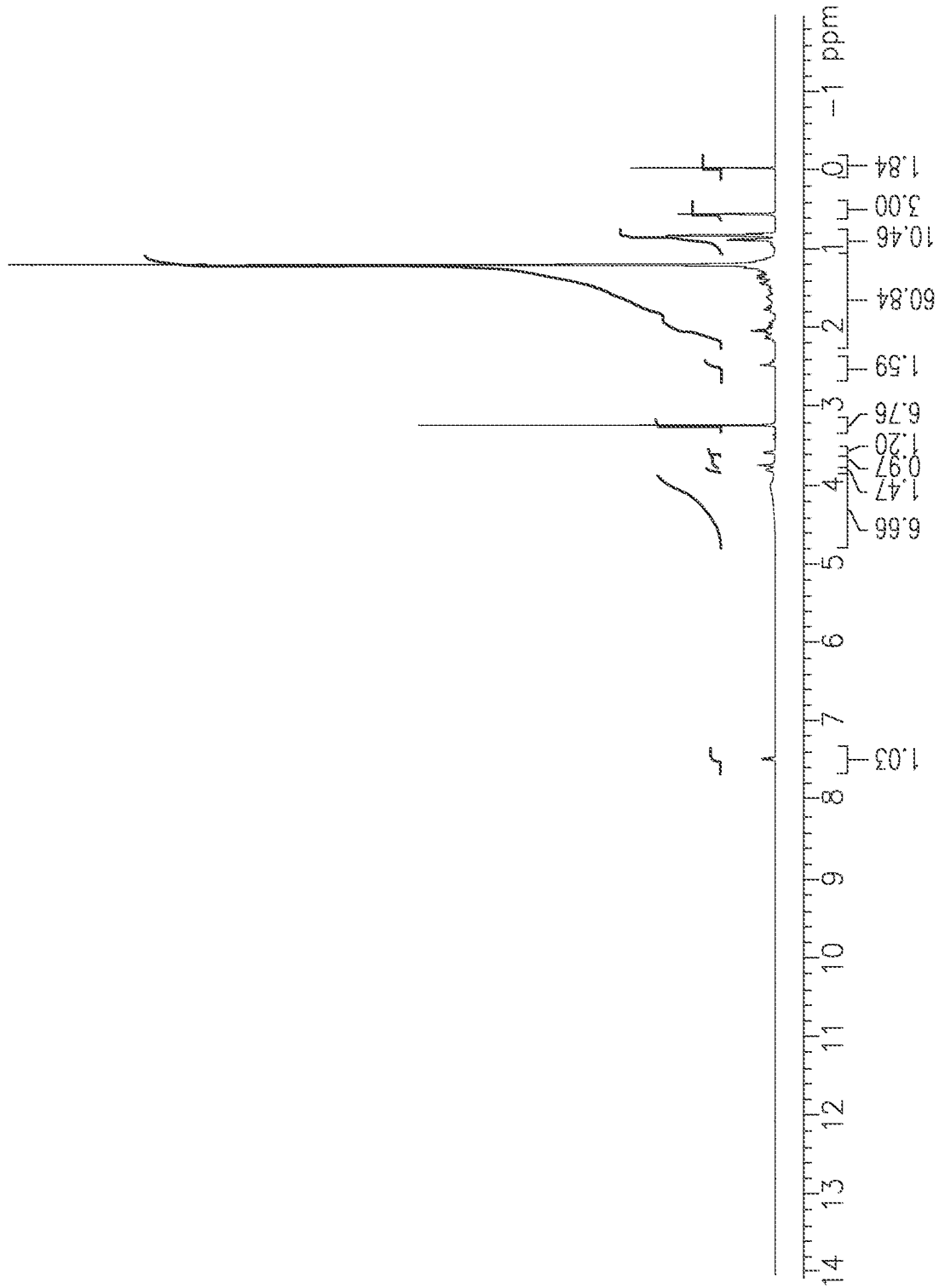
FIG. 6 illustrates a characteristic $^1$H-NMR spectrum of Aramchol tromethamine salt according to the present invention.
Figure 7:
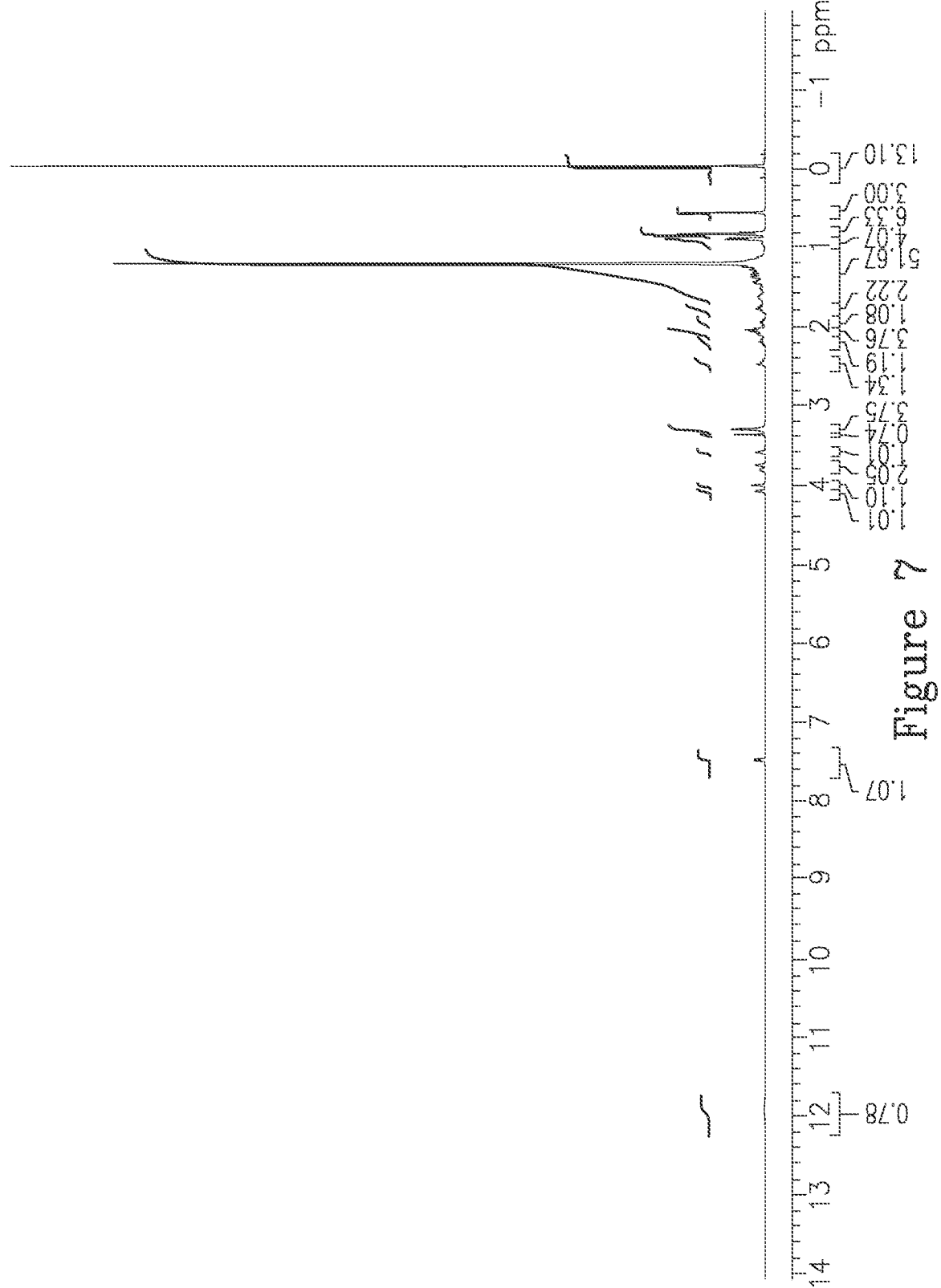
FIG. 7 illustrates a characteristic $^1$H-NMR spectrum of Aramchol free acid.

$^1$H-NMR spectra of the salts were measured, in every case the proton of the carboxylic acid function of Aramchol (located at 12 ppm on the NMR spectra) has disappeared, indicating the formation of the salts. A representative $^1$H-NMR spectrum of Aramchol N-methylglucamine salt is shown in FIG. 4. A representative $^1$H-NMR spectrum of Aramchol lysine salt is shown in FIG. 5. A representative $^1$H-NMR spectrum of Aramchol tromethamine salt is shown in FIG. 6. Shown for comparison in FIG. 7 is a representative $^1$H-NMR spectrum of Aramchol free acid.

Analytical Measurements:

The following tests were performed on the salts: LC-purity, Karl Fisher (to determine trace amounts of water in a sample) and Loss on drying (LOD) (to measure the mass % which is lost upon heating). The results show similar pattern of water content and % of mass loss among the salts (Table 3).

TABLE 3

| Entry# | LC-purity (area %) 205 nm | KF (wt %) | LOD (wt %) |
|---|---|---|---|
| Aramchol N-Methylglucamine salt | 98.84 | 1.4 | 1.4 |
| Aramchol Tromethamine salt | 99.05 | 0.9 | 1.1 |
| Aramchol Lysine salt | 96.26 | 1.3 | 1.3 |

DVS Measurements of Aramchol N-Methylglucamine

Figure 8:
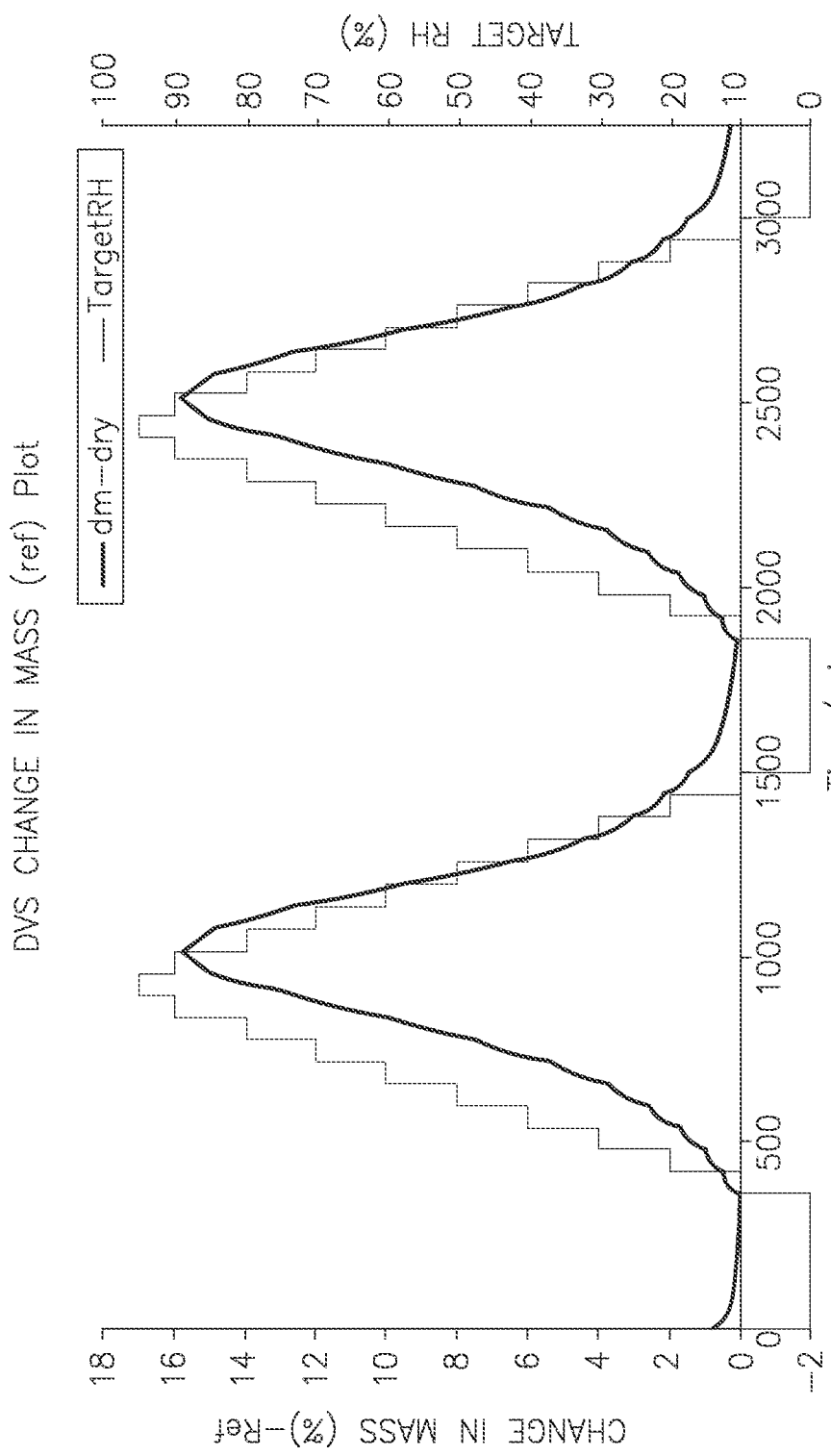
FIG. 8 illustrates a characteristic Dynamic Vapour Sorption (DVS) spectrum of Aramchol N-methylglucamine salt according to the present invention.

DVS measurements were performed to determine the sorption and desorption behavior of Aramchol N-methylglucamine salt. Sorption was measured by increasing the relative humidity (RH) with 10% per step ending at 95% RH. After completion of sorption cycle, the material was dried. XRPD was performed before and after DVS. DVS showed stepwise sorption in response to change in RH with a total mass uptake of 16%, suggesting that the material is hygroscopic. The sorption was reversible and reproducible. A representative DVS spectrum of the N-methylglucamine salt of Aramchol is depicted in FIG. 8. XRPD pattern after DVS showed amorphous material, with different peak shape and intensities (due to different particle size and shape).

Bulk and Tapped Density of Aramchol N-Methylglucamine

Measurements of tapped and bulk densities are used to predict the flow properties and compressibility of powders. These two properties are important for manufacture of solid dosage formulations, such as tablets and capsules. Compounds with low values of tapped and bulk densities may be subject to difficulties in tablet compression, and therefore may require additional processing for improving flow properties.

As shown in Table 4, Aramchol (free acid) bulk density is 0.15 g/cm$^3$ and tapped density is 0.17 g/cm$^3$. Therefore, to improve flow properties a wet granulation process is used prior to tablet compression. For Aramchol N-methylglucamine the measured bulk density is 0.57 g/mL and tapped density is 0.66 g/mL. The relatively higher values of bulk and tapped density for N-methylglucamine salt (compared to Aramchol free acid), suggest that its improved flow properties may shorten and simplify tablet production procedure by avoiding the additional step of wet granulation. This also suggests that capsule filling will be easier due to higher load of the active ingredient.

TABLE 4

Tapped and bulk densities

| Compound | Tapped density | Bulk density |
|---|---|---|
| N methylglucamine salt | 0.66 g/mL | 0.57 g/mL |
| Aramchol (free acid) | 0.17 g/cm$^3$ | 0.15 g/cm$^3$ |

Aramchol (free acid), and the three salts were filled as are, into hard HPMC (Hypromellose: Capsule size 00 (CapsCanada, ON, Canada) without taping, fill weight is presented in table 5.

TABLE 5

Fill weight of one 00 size capsule

| Aramchol (free acid) | 0.15 gram |
|---|---|
| Tromethamine salt | 0.31 gram |
| Lysine salt | 0.33 gram |
| N—Me-glucamine salt | 0.30 gram |

The fill volume demonstrate similar tapped volume for three salts

Example 4—Stability of Aramchol N-Methylglucamine

The N-methylglucamine salt of Aramchol was subjected to accelerated stability according to the following conditions:

a) Exposed to 40° C./75% RH in a closed flask as a solution b) Exposed to 40° C./75% RH in a closed container in a solid state form
c) Exposed to 40° C./75% RH in an open container in a solid state form The following parameters were determined at t=0, t=1 week, t=2 weeks: appearance, LC-purity, LC-assay (the assay is calculated against the reference which is the free acid and therefore, the results are less than 100%), water content. Table 6 summarizes the results of stability testing.

The appearance and purity remained unchanged under the investigated conditions. Impurity profiling showed neither significant change in impurities present, nor any new significant impurity formed. The calculated assay remained relatively unchanged under the investigational conditions. Water content increased under the investigational conditions and the material seemed hygroscopic. The attraction of water in the solid state form was more prominent for material stored in an open container.

TABLE 6

Summarized results of stability

|  | as a solution in a closed flask | | | In a solid state form in a closed container | | | In a solid state form in an open container | | |
| --- | --- | --- | --- | --- | --- | --- | --- | --- | --- |
|  | T = 0 | T = 2 | T = 1 | T = 0 | T = 1 | T = 2 | T = 0 | T = 1 | T = 2 |
| purity | 99.5% | 99.5% | 99.5% | 99.5% | 99.4% | 99.5% | 99.5% | 99.5% | 99.5% |
| assay | 74.7% | 74.8% | 75.3% | 74.7% | 72.8% | 74.4% | 74.7% | 76.7% | 71.9% |
| water | not applicable | | | 1.2% | 1.6% | 2.0% | 1.2% | 4.3% | 5.7% |

For Aramchol free acid, 6 months stability data have been generated at 40° C./75% relative humidity and for 12 months at real time 25° C./60% relative humidity and also at the intermediate conditions of 30° C./65% relative humidity. Under all conditions and time points there have been no significant changes to any parameters. Thus, comparison of stability of Aramchol free acid and N-methylglucamine demonstrates similar stability profile of both compounds. Moreover, while exposure of the meglumine salt of Aramchol to 40° C./75% RH caused an increase in water content, there was no change to purity values indicating that upon salt formation there is no detrimental change to the stability of Aramchol.

Example 5—Solubility of N-Methylglucamine, Tromethamine and L-Lysine Aramchol Salts Aramchol (free acid) has limited solubility in aqueous media (solubility in buffer at pH 6.0<0.001 mg/mL, max solubility of 0.66 mg/ml in FeSSIF).

The saturated solubility of N-methylglucamine, Tromethamine and L-Lysine was determined in different buffer solutions and bio-relevant media: HCl buffer pH 1.2, Acetate buffer pH 4.5, Saline pH 5.5, Phosphate buffer pH 6.5, Phosphate buffer pH 7.0, PBS pH 7.4, FaSSIF (pH 6.5), FeSSIF (pH 5.0) and demi-water (pH 7.8, was not adjusted after dissolution). Experiments were performed by slurrying a 5 mL (~150 mg) saturated solution for 30 minutes and 24 hours at 37° C. The exception was water: due to the high solubility ~1,000 mg was added to 5 mL. All experiments were performed in duplicate. Table 7 demonstrates the solubility of Aramchol salts in selected media.

TABLE 7

Overview of the solubility of selected Aramchol salts

|  |  | N-Methyl glucamine | Tromethamine | L-Lysine | Aramchol free acid |
| --- | --- | --- | --- | --- | --- |
| pH 1.2 | 30 min | 0 mg/ml | 0.02 mg/ml | 0 mg/ml | n.a. |
|  | 24 h | 0 mg/ml | 0.29 mg/ml ± 0.35 | 0 mg/ml | Not soluble |
| pH 4.5 | 30 min | 0 mg/ml | 0 mg/ml | 0 mg/ml | n.a. |
|  | 24 h | 0 mg/ml | 0 mg/ml | 0 mg/ml | Not soluble |
| pH 5.5 | 30 min | 0.04 mg/ml ± 0.06 | 0.03 mg/ml ± 0.02 | 0.05 mg/ml ± 0.02 | n.a. |
|  | 24 h | 0.00 mg/ml | 0 mg/ml | 0 mg/ml | Not soluble |
| pH 6.5 | 30 min | Gel | Gel | Gel | n.a. |
|  | 24 h | Gel | Gel | Gel | <1 µg/mL |

TABLE 7-continued

Overview of the solubility of selected Aramchol salts

|  |  | N-Methyl glucamine | Tromethamine | L-Lysine | Aramchol free acid |
|---|---|---|---|---|---|
| pH 7.0 | 30 min | 18.85 mg/ml ± 1.88 | 29.39 mg/ml ± 7.45 | 21.16 mg/ml ± 3.36 | n.a. |
|  | 24 h | Gel | Gel | Gel | Not soluble |
| pH 7.4 | 30 min | 31.83 mg/ml ± 2.35 | 22.97 mg/ml ± 3.16 | 32.72 mg/ml ± 1.80 | n.a. |
|  | 24 h | Gel | Gel | Gel | n.a. |
| FaSSIF | 30 min | Gel | Gel | Gel | 0.05 mg/ml |
|  | 24 h | Gel | Gel | Gel | 0.13 mg/ml |
| FeSSIF | 30 min | Gel | Gel | Gel | 0.66 mg/ml |
|  | 24 h | Gel | Gel | Gel | 0.31 mg/ml |
| Demi-Water | 30 min | 156.51 mg/ml ± 24.19 | 45.04 mg/ml ± 1.26 | 49.27 mg/ml ± 0.91 | n.a. |
|  | 24 h | 109.72 mg/ml ± 8.61 | Gel | Gel | Not soluble |

Data arithmetic mean ± standard deviation
n.a. not available

The results show that solubility of Aramchol salts is pH dependent: at acidic pH (pH 1.2-6.5) it is poorly soluble, with solubility increasing at pH 7 and above. At pH 7, 7.4 similar solubilities are demonstrated for all three salts. However, surprisingly, a relatively large increase in solubility (5 fold) is demonstrated for N-methylglucamine salt upon increase of pH from 7.4 (PBS) to pH 7.8 (demi-water), compared to the two other salts.

Overall, comparison of solubility between Aramchol (free acid) and salts demonstrates higher solubility for Aramchol salts at physiological relevant pH (30,000 fold increase in concentration at pH 7.4).

Example 6—In Vivo Permeability Experiments in Cannulated Rats

An in vivo permeability study of Aramchol salts was performed in male Wistar rats cannulated in the jugular vein and in the jejunum. Intestinal cannulation was performed in order to bypass protonation of Aramchol salts in acidic gastric pH. Aramchol salts solubilized in PBS (30 mg/mL) were administered to rats intestine (jejunum) in a dose of 100 mg/kg (based on free acid), via a cannula inserted into the proximal side of the jejunum. A suspension of Aramchol free acid (in PBS, 30 mg/mL) was administered via the same route and was used as control. Blood samples were withdrawn via a cannula inserted into jugular vein at predetermined time points (pre-dose, 1 hr, 2 hr, 4 hr, 8 hr, 12 hr, 24 hr post dose). Plasma concentrations of Aramchol (free acid) were measured using a liquid chromatography-tandem mass spectrometry (LC-MS-MS) method by Analyst Bioanalytical Laboratories, Israel. All PK parameters were calculated using non-compartmental analysis. Only those plasma concentrations equal to or greater than the lower limit of quantitation (LOQ) (48.66 ng/mL) were used in the analysis. Plasma concentrations <LOQ that occurred from pre-dose to the first concentration ≥LOQ were treated as 0. Actual sampling times were used for all pharmacokinetic analyses. The following PK parameters were calculated: maximum plasma concentration ($C_{max}$), time to $C_{max}$ ($T_{max}$), area under the plasma concentration-time curve from time of administration until the last plasma concentration ($AUC_{0-t}$), AUC/dose, and elimination half-life (t½). $C_{max}$ and $T_{max}$ were taken directly from the data. Area under the curve from zero to the final sample with a concentration ≥LOQ. $AUC_{0-t}$ was calculated using the linear trapezoidal method.

Figure 9:
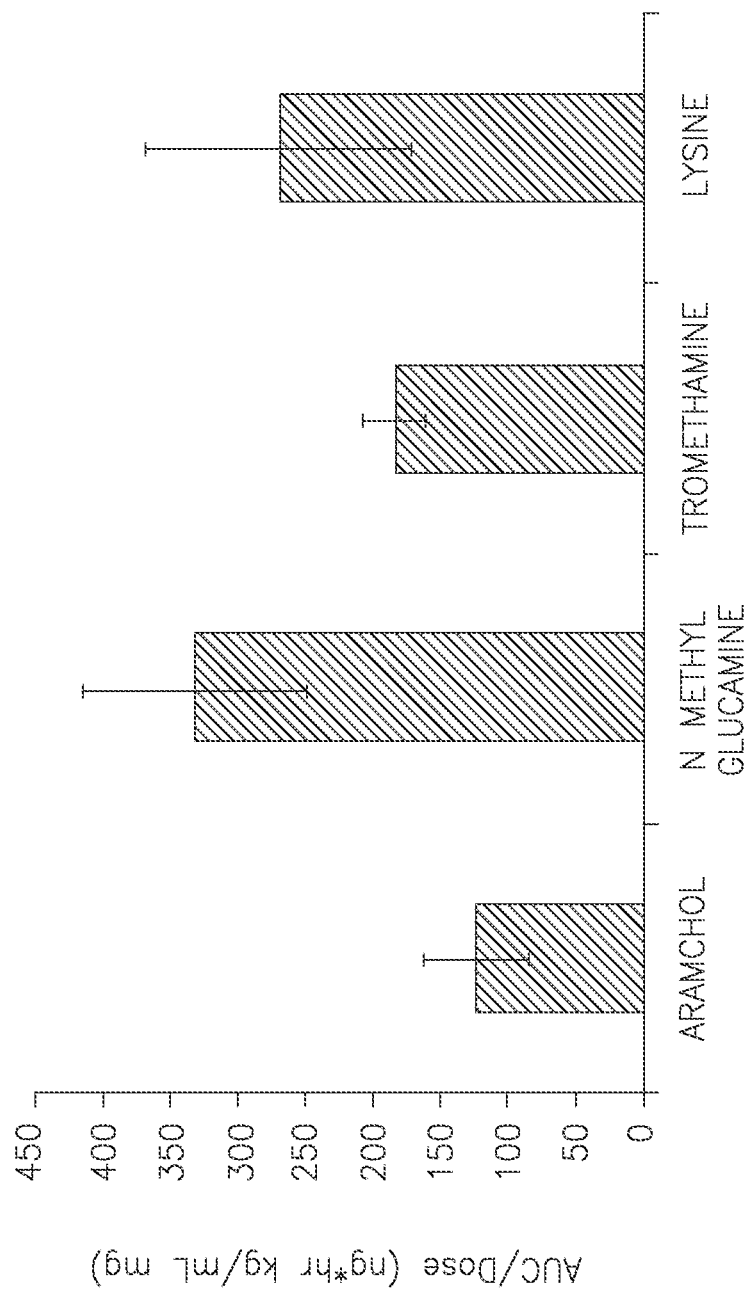
FIG. 9 AUC/dose calculated for Aramchol (free acid), N-methylglucamine, tromethamine and lysine salts. Data are arithmetic mean±standard error.

As shown in Table 8, the mean±standard error $C_{max}$ and AUC/dose of Aramchol (free acid) were lower compared to the three salts N-methylglucamine, lysine and tromethamine. A substantial increase in both AUC/dose and $C_{max}$ was observed for N-methylglucamine salt, compared to Aramchol free acid (FIG. 9). Averaged across the 2 parameters, the increase was 2.6 fold and 3.6 fold for AUC/dose and $C_{max}$, respectively.

Taken together the data show increased systemic exposure for all Aramchol salts, compared to free acid form, supporting the role of aqueous solubility in absorption of Aramchol.

TABLE 8

Summary of PK parameters for Aramchol (free acid) after intrajejunal administration of Aramchol and Aramchol salts

| Parameter | Aramchol (free acid) | N-Methylglucamine salt | Lysine salt | Tromethamine salt |
|---|---|---|---|---|
| $C_{max}$ (ng/mL) | 1362.3 ± 359.1 (5) | 5012.1 ± 1879.9 (5) | 7294.2 ± 5463.0 (5) | 2254.9 ± 208.3 (4) |
| $T_{max}$ (hr) | 4.0 (5) | 4.0 (5) [2-4] | 2.0 (5) [2-4] | 2.0 (4) [2-4] |
| $AUC_{0-t}$ (hr × ng/mL) | 12129.7 ± 3626.2 (5) | 33625.2 ± 9567.7 (5) | 26460.3 ± 9415.5 (5) | 18583.9 ± 2283.8 (4) |
| AUC/dose (hr × ng × kg/mL × mg) | 124.2 ± 38.9 (5) | 331.7 ± 82.5 (5) | 270.0 ± 99.0 (5) | 184.7 ± 22.7 (4) |
| $t_{1/2}$ (hr) | 4.5 (1) | 5.2 ± 1.0 (5) | 5.2 ± 1.0 (5) | 6.5 ± 2.4 (4) |

Arithmetic mean ± standard error (N) except for $T_{max}$ for which the median (N) [Range] is reported.
N: number of animals in each group.

CONCLUSIONS

About 30 pharmaceutically acceptable bases were screened in an effort to prepare Aramchol salts. Of them, amine-based salts were found to be suitable and in particular three salts of Aramchol have been selected as preferred salts. As demonstrated herein, the N-methylglucamine, lysine and tromethamine salts of Aramchol have been prepared and have been shown to possess advantageous properties. Several unexpected findings related to Aramchol salts in general, and the three preferred salts in particular, are summarized hereinbelow.

1) The selection of a suitable base for formation of pharmaceutically suitable Aramchol salts is not trivial. There is no clear correlation of the base molecular weight, pKa, presence of polar groups, or steric factors on salt formation.

2) Substantial solubility differences across a narrow pH range (7.0-7.8) were also unexpected. For example the three tested salts show similar solubility in pH 7 and 7.4. However, solubility of N-methylglucamine in demi-water (pH 7.8) is 5 fold higher than in pH 7.4, while for the other two salts the difference is relatively low.

3) Predicting the ability of an Aramchol salt to remain in solution is not trivial or even possible. For example, the finding that the N-methylglucamine salt shows relatively higher stability in solution compared with the other two salts was not expected or obvious (Table 7). For example, at pH=7.8 (demi-water), both the tromethamine salt and lysine salt solutions turned into gels after 24 hours, while the N-methylglucamine salt remained as a solution.

In addition, the experiments on Aramchol salts demonstrate several advantageous properties compared to the Aramchol free acid:

In vitro solubility of Aramchol salts is correlated to their in vivo absorption: The increased solubility of the three salts, compared to Aramchol free acid in physiological medium (pH buffer 7-7.8) results in increased exposure (measured by $C_{max}$ and AUC). Moreover, higher exposure of N-methylglucamine compared to lysine and tromethamine salts may be correlated to its increased propensity to remain in solution and not form precipitates or gels.

Finally, the relatively higher values of bulk and tapped density for N-methylglucamine salt (compared to Aramchol free acid) suggest that its improved flow properties may facilitate simpler tablet or capsule production. This may lead to the omission of additional processing steps such as wet granulation or other steps designed to overcome to compressibility problem of low density powders or filling limitations in hard capsules.

All references cited herein are hereby expressly incorporated by reference in their entirety. While certain embodiments of the invention have been illustrated and described, it is to be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A pharmaceutically acceptable salt of 3β-arachidylamido-7α,12α-dihydroxy-5β-cholan-24-oic acid (Aramchol), wherein said salt is an amine salt selected from the group consisting of ammonium, benzathine, trimethylglycine (betaine), ethanolamine, diethanolamine, diethylamine, arginine, lysine, choline, deanol, 2-diethylaminoethanol, N-methylglucamine (meglumine), N-ethylglucamine (eglumine), and tromethamine salt.

2. The pharmaceutically acceptable salt of claim 1, wherein the salt is N-methylglucamine (meglumine), lysine or tromethamine salt.

3. The pharmaceutically acceptable salt of claim 2, wherein the salt is N-methylglucamine (meglumine) salt.

4. The pharmaceutically acceptable salt of claim 2, wherein the salt is lysine salt.

5. The pharmaceutically acceptable salt of claim 2, wherein the salt is tromethamine salt.

6. The pharmaceutically acceptable salt of claim 1, wherein the ratio between the Aramchol and the amine is about 1:1.

7. A pharmaceutical composition in unit dosage form comprising a therapeutically effective amount of the salt of claim 1, and at least one pharmaceutically acceptable carrier, diluent, vehicle or excipient.

8. The pharmaceutical composition of claim 7, wherein said composition is in a form suitable for oral administration to a human subject.

9. The pharmaceutical composition of claim 7, wherein said composition is formulated in a form selected from the group consisting of tablets, pills, capsules, pellets, granules, powders, lozenges, sachets, cachets, patches, elixirs, suspensions, dispersions, emulsions, solutions, syrups, aerosols, ointments, soft and hard gelatin capsules, suppositories, sterile injectable solutions, sterile packaged powders and sustained-release preparations.

10. A method of treating a condition associated with fatty liver in a human subject in need thereof, comprising the step of administering to the subject the pharmaceutical composition of claim 7.

11. The method of claim 10, wherein said pharmaceutical composition is administered to said subject in a dosage regimen selected from the group consisting of: (i) once a day; (ii) 2 to 4 separate administrations per day; (iii) 2 to 4 separate administrations per week; and (iv) 2 to 4 separate administrations per month.

12. The method of claim 10, wherein the amine is N-methylglucamine (meglumine).

13. The method of claim 10, wherein said disease is Non Alcoholic Steato Hepatitis (NASH).

\* \* \* \* \*